United States Patent [19]

Bard et al.

[11] Patent Number: 5,516,653
[45] Date of Patent: May 14, 1996

[54] DNA ENCODING A HUMAN NEUROPEPTIDE Y/PEPTIDE YY/PANCREATIC POLYPEPTIDE RECEPTOR (Y4) AND USES THEREOF

[75] Inventors: Jonathan A. Bard, Wyckoff; Mary W. Walker, Elmwood Park; Theresa Branchek, Teaneck, all of N.J.; Richard L. Weinshank, New York, N.Y.

[73] Assignee: Synaptic Pharmaceutical Corporation, Paramus, N.J.

[21] Appl. No.: 176,412

[22] Filed: Dec. 28, 1993

[51] Int. Cl.$^6$ ............................ C12N 15/09; C07H 21/00; C12P 21/02
[52] U.S. Cl. .................. 435/69.1; 435/240.1; 435/240.2; 435/252.3; 435/254.11; 435/320.1; 536/23.1
[58] Field of Search ............................ 536/23.1; 435/69.1, 435/240.2, 320.1, 252.3, 254.11, 240.1; 530/350

[56] References Cited

U.S. PATENT DOCUMENTS 4,839,343   6/1993   Waeber et al. ............................ 514/12

OTHER PUBLICATIONS

Larhammar et al., The J. of Biol. Chem., vol. 267, pp. 10935, 1992.
Wahlestedt et al., Ann. N.Y. Acad. Sci, vol. 611, pp. 7, 1990.
Whitcomb, D. C., et al. Am. J. Physiol. 1990; 259:G687–G691 (Exhibit B).

Herbert Herzog, et al. PNAS 1992; 89:5794–5798 (Exhibit D).

Claes Wahlestedt, et al. Life Sciences 1991; 50:PL7–PL12 (Ehibit E).

Jan M. Lungberb, et al. The Journal of Neuroscience 1984; 4:(9):2376–2386 (Exhibit F).

*Primary Examiner*—Garnette D. Draper
*Assistant Examiner*—Sally P. Teng
*Attorney, Agent, or Firm*—John P. White

[57] ABSTRACT

This invention provides an isolated nucleic acid molecule encoding a human Y4 receptor, an isolated protein which is a human Y4 receptor, vectors comprising an isolated nucleic acid molecule encoding a human Y4 receptors, mammalian cells comprising such vectors, antibodies directed to the human Y4 receptor, nucleic acid probes useful for detecting nucleic acid encoding human Y4 receptors, antisense oligonucleotides complementary to any sequences of a nucleic acid molecule which encodes a human Y4 receptor, pharmaceutical compounds related to human Y4 receptors, and nonhuman transgenic animals which express DNA a normal or a mutant human Y4 receptor. This invention further provides methods for determining ligand binding, detecting expression, drug screening, and treatment involving the human Y4 receptor.

16 Claims, 12 Drawing Sheets

FIGURE 1A

| FIGURE 1A |
| --- |
| FIGURE 1B |
| FIGURE 1C |
| FIGURE 1D |
| FIGURE 1E |

```
            -80               -60               -40
             .                 .                 .
 -28  AGTATTGTTTGTCTGTGTTTGCCTTGTAGGGCGTCATCCCTCAAGTGTATCACTTAGTTCAA    31

.                 .                 .
            -20                -1                20
  32  GAGTCCTGGAATCTTTTCACATCCACTATGAACACCTCTCACCTCCTGGCCTTGCTGCTC    91
  -8                           M  N  T  S  H  L  L  A  L  L  L    11

.                 .                 .
            40                 60                80
  92  CCAAAATCTCCACAAGGTGAAAACAGAAGCAAACCCCTGGGCACCCCATACAACTTCTCT   151
  12   P  K  S  P  Q  G  E  N  R  S  K  P  L  G  T  P  Y  N  F  S    31

.                 .                 .
            100                120               140
 152  GAACATTGCCAGGATTCCGTGGACGTGATGGTCTTCATCGTCACTTCCTACAGCATTGAG   211
  32   E  H  C  Q  D  S  V  D  V  M  V  F  I  V  T  S  Y  S  I  E    51

.                 .                 .
            160                180               200
 212  ACTGTCGTGGGGGTCCTGGGTAACCTCTGCCTGATGTGTGTGACTGTGAGGCAGAAGGAG   271
  52   T  V  V  G  V  L  G  N  L  C  L  M  C  V  T  V  R  Q  K  E    71
```

FIGURE 1B

```
                     220                240                260
272 AAAGCCAACGTGACCAACCTGCTTATCGCCAACCTGGCCTTCTCTGACTTCCTCATGTGC 331
 72  K  A  N  V  T  N  L  L  I  A  N  L  A  F  S  D  F  L  M  C   91

280                300                320
332 CTCCTCTGCCAGCCGCTGACCGCCGTCTACACCATCATGGACTACTGGATCTTTGGAGAG 391
 92  L  L  C  Q  P  L  T  A  V  Y  T  I  M  D  Y  W  I  F  G  E  111

340                360                380
392 ACCCTCTGCAAGATGTCGGCCTTCATCCAGTGCATGTCGGTGACGGTCTCCATCCTCTCG 451
112  T  L  C  K  M  S  A  F  I  Q  C  M  S  V  T  V  S  I  L  S  131

400                420                440
452 CTCGTCGTCGTGGCCCTGGAGAGGCATCAGCTCATCATCAACCCAACAGGCTGGAAGCCC 511
132  L  V  V  A  L  E  R  H  Q  L  I  I  N  P  T  G  W  K  P  151

460                480                500
512 AGCATCTCACAGGCCTACCTGGGGATTGTGCTCATCTGGGTCATTGCCTGTGTCCTCTCC 571
152  S  I  S  Q  A  Y  L  G  I  V  L  I  W  V  I  A  C  V  L  S  171
```

FIGURE 1C

```
572  CTGCCCTTCCTGGCCAACAGCATCCTGGAGAATGTCTTCCACAAGAACCACTCCAAGGCT  631
172   L   P   F   L   A   N   S   I   L   E   N   V   F   H   K   N   H   S   K   A   191
              520                 540                 560

632  CTGGAGTTCCTGGCAGATAAGGTGGTCTGTACCGAGTCCTGGCCACTGGCTCACCACCGC  691
192   L   E   F   L   A   D   K   V   V   C   T   E   S   W   P   L   A   H   H   R   211
              580                 600                 620

692  ACCATCTACACCACCTTCCTGCTCCTCTTCCAGTACTGCCTCCCACTGGGCTTCATCCTG  751
212   T   I   Y   T   T   F   L   L   L   F   Q   Y   C   L   P   L   G   F   I   L   231
              640                 660                 680

752  GTCTGTTATGCACGGATCTACTACCGGCGCCTGCAGAGGCAGGGGCGTGTTTCACAAGGGC  811
232   V   C   Y   A   R   I   Y   Y   R   R   L   Q   R   Q   G   R   V   F   H   K   G  251
              700                 720                 740

812  ACCTACAGCTTGCGAGCTGGGCACATGAAGCAGGTCAATGTGGTCGTGGTGATGGTG  871
252   T   Y   S   L   R   A   G   H   M   K   Q   V   N   V   V   L   V   V   M   V   271
              760                 780                 800
```

FIGURE 1D

```
872  GTGGCCTTTGCCGTGCTCTGGCTGCCTCTGCATGTGTTCAACAGCCTGGAAGACTGGCAC  931
272   V   A   F   A   V   L   W   L   P   L   H   V   F   N   S   L   E   D   W   H   291

932  CATGAGGCCATCCCCATCTGCCACGGGAACCCTCATCTTCTTAGTGTGCCACTTGCTTGCC  991
292   H   E   A   I   P   I   C   H   G   N   L   I   F   L   V   C   H   L   L   A   311

992  ATGGCCTCCACCTGCGTCAACCCATTCATCTATGGCTTTCTCAACACCAACTTCAAGAAG  1051
312   M   A   S   T   C   V   N   P   F   I   Y   G   F   L   N   T   N   F   K   K   331

1052 GAGATCAAGGCCCTGGTGCTGACTTGCCAGCAGAGCCCCCTGGAGGAGTCGGAGCAT    1111
332   E   I   K   A   L   V   L   T   C   Q   Q   S   A   P   L   E   E   S   E   H   351

1112 CTGCCCCTGTCCACAGTACATACGGAAGTCTCCAAAGGGTCCCTGAGGCTAAGTGGCAGG  1171
352   L   P   L   S   T   V   H   T   E   V   S   K   G   S   L   R   L   S   G   R   371
```

FIGURE 1E

```
1172  TCCAATCCCATTTAACCAGGTCTAGGTCTTCCCTGCCATGTCCCTTGCCAGGCTCTTC  1231
372   S   N   P   I   *                                              375

1232  CACTTAGCTAAGTGGGCACACTGCAAGCTGGGGTGGCACCCCAGCATTCCTGGCTTTCTG  1291
```

FIGURE 2A

|  | FIGURE 2A |
|---|---|
|  | FIGURE 2B |
|  | FIGURE 2C |

```
                                                                    50
     1
hp25a    MNTSHLLALL LPKSPQGENR SKPLGTPYNF SEHCQDSVDV MVFIVTSYSI
human Y1 MN.STLFSQV ENHSVHSNFS EKNAQLLAFE NDDCHLPLAM IFTLALAYGA
rat Y1   MN.STLFSRV ENYSVHYNVS E.NSPFLAFE NDDCHLPLAV IFTLALAYGA
mouse Y1 MN.STLFSKV ENHSIHYNAS E.NSPLLAFE NDDCHLPLAV IFTLALAYGA I                                            100
     51                                                     II
hp25a    ETVVGVLGNL CLMCVTVRQK EKANVTNLLI ANLAFSDFLM CLLCQPLTAV
human Y1 VIILGVSGNL ALIIIILKQK EMRNVTNILI VNLSFSDLLV AIMCLPFTFV
rat Y1   VIILGVSGNL ALIIIILKQK EMRNVTNILI VNLSFSDLLV AVMCLPFTFV
mouse Y1 VIILGVSGNL ALIIIILKQK EMRNVTNILI VNLSFSDLLV AVMCLPFTFV 150
     101             III
hp25a    YTIMDYWIFG ETLCKMSAFI QCMSVTVSIL SLVLVALERH QLIINPTGWK
human Y1 YTLMDHWVFG EAMCKLNPFV QCVSITVSIF SLVLIAVERH QLIINPRGWR
rat Y1   YTLMDHWVFG ETMCKLNPFV QCVSITVSIF SLVLIAVERH QLIINPRGWR
mouse Y1 YTLMDHWVFG ETMCKLNPFV QCVSITVSIF SLVLIAVERH QLIINPRGWR IV                                                200
     151
hp25a    PSISQAYLGI VLIWVIACVL SLPFIANSIL ENVFHKNHSK ALEFLADKVV
human Y1 PNNRHAYVGI AVIWVLAVAS SLPFLIYQVM TDEPFQNVT. .LDAYKDKYV
rat Y1   PNNRHAYIGI TVIWVLAVAS SLPFVIYQIL TDEPFQNVS. .LAAFKDKYV
mouse Y1 PNNRHAYIGI TVIWVLAVAS SLPFVIYQIL TDEPFQNVS. .LAAFKDKYV
```

```
        201                                                      250
hp25a    CTESWPLAHH RTIYTTFLEL FQYCLPLGFI LVCYARIYRR LQRGRVFHK
human Y1 CFDQFPSDSH RLSYTTLLEV LQYFGPLCFI FICYFKIYIR LKRRNNMMDK
rat Y1   CFDKFPSDSH RLSYTTLLEV LQYFGPLCFI FICYFKIYIR LKRRNNMMDK
mouse Y1 CFDKFPSDSH RLSYTTLLEV LQYFGPLCFI FICYFKIYIR LKRRNNMMDK
                              └──────── V ────────┘

251                                                      300
hp25a    GTYS.LRAGH MKQVNVVLVV MVVAFAVLWL PLHVFNSLED WHHEAIPICH
human Y1 MRDNKYRSSE TKRINIMLLS IVVAFAVCWL PLTIFNTVFD WNHQIIATCN
rat Y1   IRDSKYRSSE TKRINVMLLS IVVAFAVCWL PLTIFNTVFD WNHQIIATCN
mouse Y1 IRDSKYRSSE TKRINIMLLS IVVAFAVCWL PLTIFNTVFD WNHQIIATCN
                              └──── VI ────┘

301                                                      350
hp25a    GNLIFLVCHL LAMASTCVNP FIYGFLNTNF KKEIKALVLT CQQSAPLEES
human Y1 HNLLFLLCHL TAMISTCVNP IFYGFLNKNF QRDLQFFFNF CDFRSRDDDY
rat Y1   HNLLFLLCHL TAMISTCVNP IFYGFLNKNF QRDLQFFFNF CDFRSRDDDY
mouse Y1 HNLLFLLCHL TAMISTCVNP IFYGFLNKNF QRDLQFFFNF CDFRSRDDDY
                    └─ VII ─┘
```

FIGURE 2C

```
         351                                            388
hp25a    EHLPLSTVHT EVSKGSERLS GRSNPI*.... ..........
human Y1 ETIAMSTMHT DVSKTSLKQA SPVAFKKINN NDDNEKI*
rat Y1   ETIAMSTMHT DVSKTSLKQA SPVAFKKISM N.DNEKI*
mouse Y1 ETIAMSTMHT DVSKTSLKQA SPVAFKKISM N.DNEKV*
```

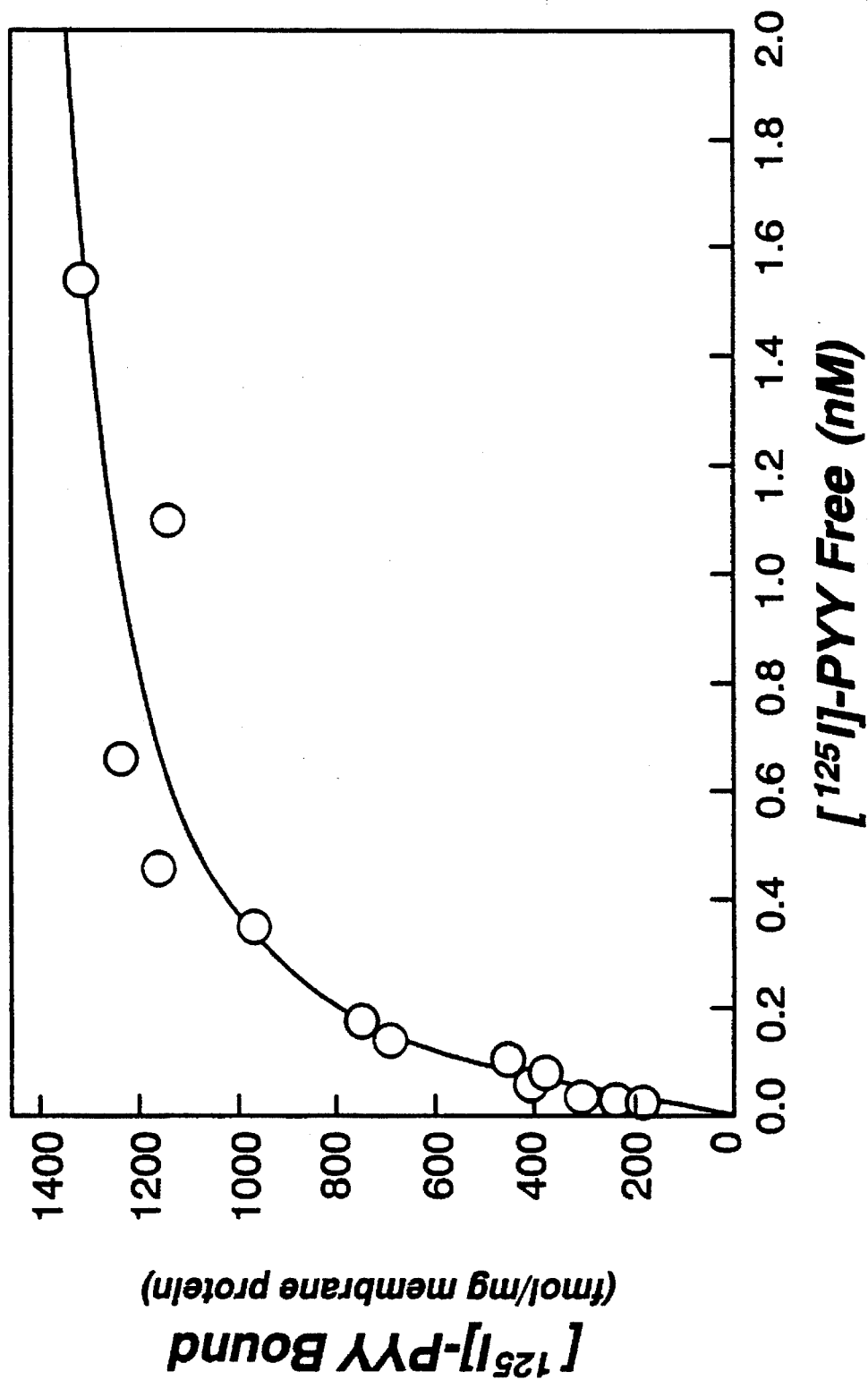

DNA ENCODING A HUMAN NEUROPEPTIDE Y/PEPTIDE YY/PANCREATIC POLYPEPTIDE RECEPTOR (Y4) AND USES THEREOF

BACKGROUND OF THE INVENTION

Throughout this application, various publications are referenced in parenthesis by Author and year. Full citations for these references may be found at the end of the specification immediately preceding the claims. The disclosure of these publications is hereby incorporated by reference into this application to describe more fully the art to which this invention pertains.

Neuropeptides are small peptides originating from large precursor proteins synthesized by peptidergic neurons and endocrine/paracrine cells. They hold promise for treatment of neurological, psychiatric, and endocrine disorders (De Wied, 1990). Often the precursors contain multiple biologically active peptides. There is great diversity of neuropeptides in the brain caused by alternative splicing of primary gene transcripts and differential precursor processing. The neuropeptide receptors serve to discriminate between ligands and to activate the appropriate signals. Thus, it is expected that the receptors for neuropeptides consist of a large number of members.

Neuropeptide Y (NPY), a 36-amino acid peptide, is the most abundant neuropeptide to be identified in mammalian brain. NPY is an important regulator in both the central and peripheral nervous systems (Heilig et al., 1990) and influences a diverse range of physiological parameters, including effects on psychomotor activity, food intake, central endocrine secretion, and vasoactivity in the cardiovascular system. High concentrations of NPY are found in the sympathetic nerves supplying the coronary, cerebral, and renal vasculature and has contributed to vasoconstriction. NPY binding sites have been identified in a variety of tissues, including spleen (Lundberg et al., 1988), intestinal membranes, brain (Hinson et al., 1988), aortic smooth muscle (Mihara et al., 1989), kidney, testis, and placenta (Dumont et al., 1992). In addition, binding sites have been reported in a number of rat and human cell lines (eg. Y1 in SK-N-MC, MC-IXC, CHP-212, and PC12 cells; Y2 in SK-N-Be(2), CHP-234, and SMS-MSN)(Aakerlund et al., 1990; Grundemar et al., 1993).

NPY forms a family (called the pancreatic polypeptide family) together with pancreatic polypeptide (PP) and peptide YY (PYY) which all consist of 36 amino acids and have a common tertiary structure, the so-called PP-fold (Glover et al., 1985). Specific features of this family include a polyproline helix in residues 1 through 8, β-turn in residues 9 through 14, an α-helix in residues 15 through 30, an outward-projecting C-terminus in residues 30 through 36, and a carboxy terminal amide which appears to be critical for biological activity (Schwartz et al., 1990). The C-terminal amidated residue of these peptides is essential for biological activity (Wahlestedt et al., 1986). Studies with peptide fragments of NPY have indicated that multiple NPY receptor subtypes exist (Wahlestedt et al., 1986). Three major NPY receptor subtypes (Y1, Y2 and Y3) have been defined by pharmacological criteria, with a fourth "atypical" Y1 receptor that has been proposed to regulate feeding behavior. The only NPY receptor which has been cloned to date is the Y1 receptor gene, from mouse (Eva et al., 1992), rat (Eva et al., 1990), and human (Larhammar et al., 1992). One of the key pharmacological features which distinguish Y1 and Y2 is the fact that the Y1 receptor (and not the Y2 receptor) responds to an analog of NPY modified at residues 31 and 34 ([Leu31,Pro34]NPY), whereas the Y2 receptor (and not the Y1 receptor) has high affinity for the NPY peptide carboxyl-terminal fragment NPY-(13- 36)(Wahlstedt et al., 1986; Fuhlendorff et al., 1990).

Receptor genes for the other two structurally related peptides, peptide YY (PYY) and pancreatic polypeptide (PP), also have not been cloned. Peptide YY occurs mainly in endocrine cells in the lower gastrointestinal tract (Bottcher et al., 1984). Receptors for PYY were first described in the rat small intestine (Laburthe et al., 1986). This receptor has been defined as PYY-preferring because it displays a 5–10 fold higher affinity for PYY than for NPY (Laburthe et al., 1986; Laburthe, 1990). Recently, a cell line, PKSV-PCT, derived from the proximal tubules of kidneys, has been described to express receptors for PYY (Voisin et al., 1993). Pancreatic polypeptide is predominantly located in endocrine cells of the pancreatic islets (Alumets et al., 1978). PP inhibits pancreatic exocrine secretion and gall bladder contraction (Schwartz, 1983). Interestingly, PP does not appear to be synthesized in or localized to the central nervous system (Di Maggio et al., 1985), but selective PP binding sites have been found in various brain areas, such as the-area postrema and adjacent nuclei, regions permeable at the bloodbrain barrier (Whitcomb et al., 1990). PP receptors have a much higher affinity for PP than for NPY or PYY (Inui et al., 1990). PP has been shown to bind with high affinity to binding sites on a pheochromocytoma cell line, PC12 (Schwartz et al., 1987). The rank order of affinity for the pharmacologically defined receptors of NPY and related peptides are listed in Table I.

Using an homology screening approach to clone novel NPY receptor genes, we describe here the isolation and characterization of a novel NPY/PYY/PP receptor clone which we have designated Y4. The Y4 receptor appears to have a unique pharmacological profile, relative to other NPY-related receptors, exhibiting highest affinity for pancreatic polypeptide itself. This receptor clone will enable us to further examine the possibility of receptor diversity and the existence of multiple subtypes within this family of receptors. These could then serve as invaluable tools for drug design for several pathophysiological conditions such as memory loss, depression, anxiety, epilepsy, pain, hypertension, and sleep and eating disorders.

SUMMARY OF THE INVENTION

This invention provides an isolated nucleic acid molecule encoding a human Y4 receptor.

This invention also provides an isolated protein which is a human Y4 receptor.

This invention provides a vector comprising an isolated nucleic acid molecule encoding a human Y4 receptor.

This invention also provides vectors such as plasmids comprising a DNA molecule encoding a human Y4 receptor, adapted for expression in a bacterial cell, a yeast cell, an insect cell or a mammalian cell which additionally comprise the regulatory elements necessary for expression of the DNA in the bacterial, yeast, insect or mammalian cells operatively linked to the DNA encoding the Y4 receptor as to permit expression thereof.

This invention provides a mammalian cell comprising a DNA molecule encoding a human Y4 receptor.

This invention provides a method for determining whether a ligand not known to be capable of binding to a human Y4 receptor can bind to a human Y4 receptor which comprises contacting a mammalian cell comprising an isolated DNA molecule encoding a human Y4 receptor with the ligand under conditions permitting binding of ligands known to bind to a Y4 receptor, detecting the presence of any of the ligand bound to a human Y4 receptor, and thereby determining whether the ligand binds to a human Y4 receptor.

This invention also provides a method for determining whether a ligand not known to be a human Y4 receptor agonist is capable of binding to the human Y4 receptor and functionally activate the human Y4 receptor which comprises contacting a mammalian cell expressing the human Y4 receptor with the ligand under conditions permitting the activation of a functional response, and detecting by means of a bioassay from the mammalian cell, such as a second messenger response, an increase in Y4 receptor activity, and thereby determining whether the ligand is a human Y4 receptor agonist.

This invention further provides a method for determining whether a ligand not known to be a human Y4 receptor antagonist is capable of binding to the human Y4 receptor and functionally inhibit the human Y4 receptor activity which comprises contacting a mammalian cell expressing the human Y4 receptor with the ligand under conditions permitting the activation of a functional response, and detecting by means of a bioassay from the mammalian cell, such as a second messenger response, a decrease in Y4 receptor activity, and thereby determining whether the ligand is a human Y4 receptor antagonist.

This invention further provides a method of screening drugs to identify drugs which specifically interact with, and bind to, the human Y4 receptor on the surface of a cell which comprises contacting a mammalian cell comprising an isolated DNA molecule encoding a human Y4 receptor with a plurality of drugs, determining those drugs which bind to the mammalian cell, and thereby identifying drugs which specifically interact with, and bind to, a human Y4 receptor.

This invention also provides a method of screening drugs to identify which act as agonists of the human Y4 receptor on the surface of a cell which comprises contacting a mammalian cell expressing human Y4 receptor with a plurality of drugs, determining those drugs which activate the receptor in the mammalian cell using a bioassay such as a second messenger assays, and thereby identifying drugs which specifically interact with, and activate the human Y4 receptor.

This invention also provides a method of screening drugs to identify drugs which act as antagonists of the human Y4 receptor on the surface of a cell which comprises contacting a mammalian cell expressing the human Y4 receptor with a plurality of drugs in the presence of a known human Y4 receptor agonist such as NPY, determining those drugs which inhibit the activation of the receptor in the mammalian cell using a bioassay such as a second messenger assays, and thereby identifying drugs which act as antagonists of the human Y4 receptor.

This invention provides a nucleic acid probe comprising a nucleic acid molecule of at least 15 nucleotides capable of specifically hybridizing with a unique sequence included within the sequence of a nucleic acid molecule encoding a human Y4 receptor.

This invention also provides a method of detecting expression of the Y4 receptor on the surface of a cell by detecting the presence of mRNA coding for a Y4 receptor which comprises obtaining total mRNA from the cell and contacting the mRNA so obtained with a nucleic acid probe comprising a nucleic acid molecule of at least 15 nucleotides capable of specifically hybridizing with a unique sequence included within the sequence of a nucleic acid molecule encoding a human Y4 receptor under hybridizing conditions, detecting the presence of mRNA hybridized to the probe, and thereby detecting the expression of the Y4 receptor by the cell.

This invention provides an antisense oligonucleotide having a sequence capable of binding specifically with any sequences of an mRNA molecule which encodes a human Y4 receptor so as to prevent translation of the mRNA molecule.

This invention provides an antibody directed to a human Y4 receptor.

This invention provides a transgenic nonhuman mammal expressing DNA encoding a human Y4 receptor. This invention further provides a transgenic nonhuman mammal whose genome comprises antisense DNA complementary to DNA encoding a human Y4 receptor so placed as to be transcribed into antisense mRNA which is complementary to mRNA encoding a Y4 receptor and which hybridizes to mRNA encoding a Y4 receptor thereby reducing its translation.

This invention provides a method of determining the physiological effects of expressing varying levels of human Y4 receptors which comprises producing a transgenic nonhuman animal whose levels of human Y4 receptor expression are varied by use of an inducible promoter which regulates human Y4 receptor expression.

This invention also provides a method of determining the physiological effects of expressing varying levels of human Y4 receptors which comprises producing a panel of transgenic nonhuman animals each expressing a different amount of human Y4 receptor.

This invention provides a method for diagnosing a predisposition to a disorder associated with the expression of a specific human Y4 receptor allele which comprises: a. obtaining DNA of subjects suffering from the disorder; b. performing a restriction digest of the DNA with a panel of restriction enzymes; c. electrophoretically separating the resulting DNA fragments on a sizing gel; d. contacting the resulting gel with a nucleic acid probe capable of specifically hybridizing to DNA encoding a human Y4 receptor and labelled with a detectable marker; e. detecting labelled bands which have hybridized to the DNA encoding a human Y4 receptor labelled with a detectable marker to create a unique band pattern specific to the DNA of subjects suffering from the disorder; f. preparing DNA obtained for diagnosis by steps a–e; and g. comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method of preparing the isolated Y4 receptor which comprises inducing cells to express Y4 receptor, recovering the receptor from the resulting cells and purifying the receptor so recovered.

This invention also provides a method of preparing the isolated Y4 receptor which comprises inserting nucleic acid encoding Y4 receptor in a suitable vector, inserting the resulting vector in a suitable host cell, recovering the receptor produced by the resulting cell, and purifying the receptor so recovered.

This invention provides an antisense oligonucleotide having a sequence capable of binding specifically with any sequences of an mRNA molecule which encodes the Y4 receptor so as to prevent translation of mRNA molecules which encode the Y4 receptor.

This invention also provides a transgenic nonhuman mammal expressing DNA encoding a human Y4 receptor.

This invention further provides a transgenic nonhuman mammal comprising a homologous recombination knockout of the native Y4 receptor.

This invention also provides a method of determining the physiological effects of expressing varying levels of a receptor which comprises producing a transgenic nonhuman animal whose levels of human Y4 receptor expression are varied by use of an inducible promoter which regulates receptor expression.

This invention also provides a method of determining the physiological effects of expressing varying levels of a human Y4 receptor which comprises producing a panel of transgenic nonhuman animals each expressing a different amount of the receptor.

This invention further provides a transgenic nonhuman mammal whose genome comprises antisense DNA complementary to DNA encoding a human Y4 receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to the Y4 receptor can bind to the receptor which comprises contacting a mammalian cell comprising an isolated DNA molecule encoding the Y4 receptor with the ligand under conditions permitting binding of ligands known to bind to the receptor, detecting the presence of any of the ligand bound to the Y4 receptor, and thereby determining whether the ligand binds to the Y4 receptor.

BRIEF DESCRIPTION OF THE FIGURES

FIGS. 1A–1E

Nucleotide Sequence and Deduced Amino Acid Sequence of a Novel Human hp25a Neuropeptide Receptor (Sequence I.D. Nos. 1 and 2). Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionine (M), respectively.

FIGS. 2A–2C

Sequence Alignment of the Human hp25a clone with human Y1, rat Y1, and mouse Y1 receptor genes. The deduced amino acid sequence of the human hp25a (Y4) receptor (first line), from the starting methionine (M) to the stop codon (*), is aligned with the human Y1 receptor clone (Larhammar et al., 1992), rat Y1 receptor clone (Eva et al., 1990), and mouse Y1 receptor clone (Eva et al., 1992). Hyphens represent added spaces necessary for proper alignment. Gray shading indicates residues in receptor clones which are identical to hp25a. Numbers above amino acid sequences correspond to amino acid positions of hp78a, starting with the initiating methionine (M) and ending with the termination codon (*), and including spaces to account for proper alignment.

FIG. 3

Equilibrium binding of $^{125}$I-PYY to membranes from COS-7 cells transiently expressing hp25a receptors. Membranes were incubated with $^{125}$I-PYY for the times indicated, in the presence or absence of 100 nM human PP. Specific binding, B, was plotted against time, t, to obtain the maximum number of equilibrium binding sites, $B_t$, and observed association rate, $K_{obs}$, according to the equation, $B=B_t*(1-e^{-(kobs*t)})$. Binding is shown as the percentage of total equilibrium binding, $B_t$, determined by nonlinear regression analysis. Data are representative of three independent experiments, with each point measured in triplicate.

FIG. 4A

Saturable equilibrium binding of $^{125}$I-PYY to membranes from COS-7 cells transiently expressing hp25a receptors. Membranes were incubated with $^{125}$I-PYY ranging in concentration from 0.003 nM to 2 nM, in the presence or absence of 100 nM human PP.

FIG. 4B

Figure 4B:
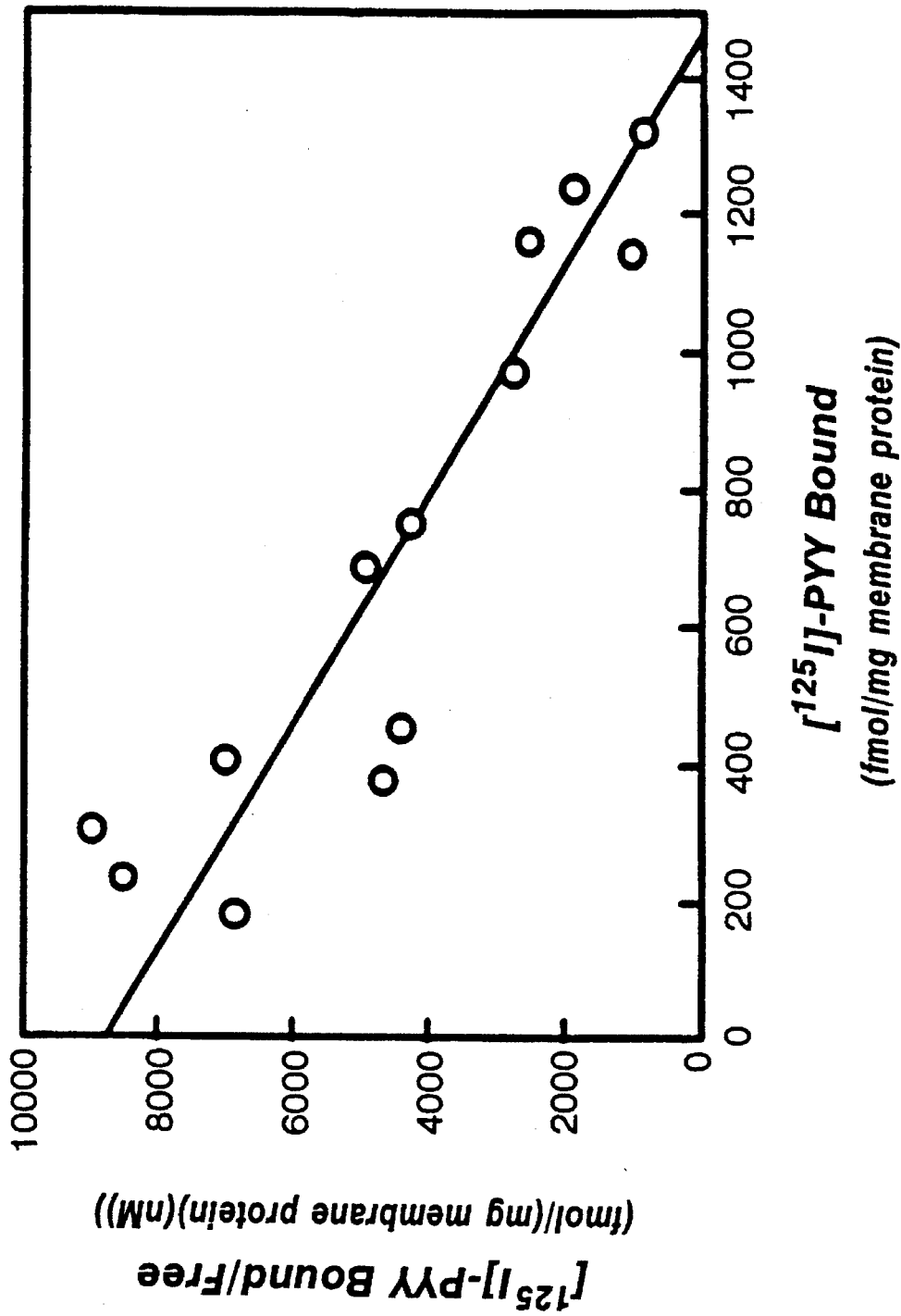

Specific binding of the $^{125}$I-PYY to membranes from COS-7 cells transiently expressing hp25a receptors under the conditions described in FIG. 4A was plotted against the free $^{125}$I-PYY concentration, [L], to obtain the maximum number of saturable binding sites, $B_{max}$, and the $^{125}$I-PYY equilibrium dissociation constant, $K_d$, according to the binding isotherm, $B=B_{max}[L]/([L]+K_d)$. Specific binding is shown for data from a representative of four independent experiments, with each point measured in quadruplicate.

FIG. 5

Competitive displacement of $^{125}$I-PYY from COS-7 cells transiently expressing hp25a receptors. Membranes were incubated with $^{125}$I-PYY and increasing concentrations of peptide competitors. $IC_{50}$ values corresponding to 50% displacement were determined by nonlinear regression analysis and converted to $K_i$ values according to the equation, $K_i=IC_{50}/(1+[L]/K_d)$, where [L] is the $^{125}$I-PYY concentration and $K_d$ is the equilibrium dissociation constant of $^{125}$I-PYY. Data are representative of at least two independent experiments, with each point measured once or in duplicate. Rank orders of affinity for these and other compounds are listed separately in Table 2.

DETAILED DESCRIPTION OF THE INVENTION

This invention provides isolated nucleic acid molecules which encode the human Y4 receptor. As used herein, the term Y4 receptor encompasses any amino acid sequence, polypeptide or protein having substantially the same pharmacology provided subject human Y4 receptor as shown in Tables 1–2 and FIGS. 3–5. As described herein the human Y4 receptor has a pharmacological profile that differs from any known Neuropeptide Y receptor subtype (i.e. Y1, Y2 and Y3), Neuropeptide YY receptor, and pancreatic polypeptide receptor, and is therefore designated as the human Y4 receptor.

The only NPY receptor which has been cloned to date is the Y1 receptor gene, from mouse (Eva et al., 1992), rat (Eva et al., 1990), and human (Larhammar et al., 1992). The Y4 receptor's greatest homology with any known receptor disclosed in the Genbank/EMBL databases is a 42% overall amino acid identity with the human Y1 receptor.

This invention provides an isolated nucleic acid molecule encoding a human Y4 receptor. As used herein, the term "isolated nucleic acid molecule" means a nucleic acid molecule that is, a molecule in a form which does not occur in nature. Examples of such an isolated nucleic acid molecule are an RNA, cDNA, or isolated genomic DNA molecule encoding a human Y4 receptor. The human Y4 receptor has an amino acid sequence substantially the same as the deduced amino acid sequence shown in FIGS. 1A–1E and any human receptor having substantially the same amino acid sequence as shown in FIGS. 1A–1E is by definition a human Y4 receptor. One means of isolating a human Y4 receptor is to probe a human genomic library with a natural or artificially designed DNA probe, using methods well known in the art. DNA probes derived from the human receptor gene Y4 are particularly useful probes for this purpose. DNA and cDNA molecules which encode human Y4 receptors may be used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clones, and other stability, processing, transcription, translation, and tissue specificity-determining regions from the 3' and 5' untranslated regions of the isolated genes are thereby obtained. Examples of a nucleic acid molecule are an RNA, cDNA, or isolated genomic DNA molecule encoding a human Y4 receptor. Such molecules may have coding sequences substantially the same as the coding sequence shown in FIGS. 1A–1E. The DNA molecule of FIGS. 1A–1E encodes the sequence of the human Y4 receptor gene.

This invention further provides a cDNA molecule of encoding a human Y4 receptor having a coding sequence substantially the same as the coding sequence shown in FIGS. 1A–1E. This molecule is obtained by the means described above.

This invention also provides an isolated protein which is a human Y4 receptor. As used herein, the term "isolated protein means a protein molecule free of other cellular components. An example of such protein is an isolated protein having substantially the same amino acid sequence as the amino acid sequence shown in FIG. 1 which is a human Y4 receptor. One means for obtaining isolated Y4 receptor is to express DNA encoding the receptor in a suitable host, such as a bacterial, yeast, insect or mammalian cell, using methods well known in the art, and recovering the receptor protein after it has been expressed in such a host, again using methods well known in the art. The receptor may also be isolated from cells which express it, in particular from cells which have been transfected with the expression vectors described below in more detail.

This invention provides a vector comprising an isolated nucleic acid molecule such as DNA, RNA, or cDNA encoding a human Y4 receptor. Examples of vectors are viruses such as bacteriophages (such as phage lambda), animal viruses (such as Herpes virus, Murine Leukemia virus, and Baculovirus), cosmids, plasmids (such as pUC18, available from Pharmacia, Piscataway, N.J.), and other recombination-vectors. Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available. A specific example of such plasmids is a plasmid comprising cDNA having a coding sequence substantially the same as the coding sequence shown in FIGS. 1A–1E and designated clone hp25a (Seq. I.D. No. 1).

This invention also provides vectors comprising a DNA molecule encoding a human Y4 receptor, adapted for expression in a bacterial cell, a yeast cell, insect or a mammalian cell which additionally comprise the regulatory elements necessary for expression of the DNA in the bacterial, yeast, insect or mammalian cells operatively linked to the DNA encoding a human Y4 receptor as to permit expression thereof. DNA having coding sequences substantially the same as the coding sequence shown in FIGS. 1A–1E may usefully be inserted into the vectors to express human Y4 receptors. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Furthermore, an insect expression vector, such as recombinant Baculovirus, uses the polyhedrin gene expression signals for expression of the inserted gene in insect cells. Such vectors may be obtained commercially or assembled from the sequences described by methods well known in the art, for example the methods described above for constructing vectors in general. Expression vectors are useful to produce cells that express the receptor. Certain uses for such cells are described in more detail below.

This invention further provides a plasmid adapted for expression in a bacterial, yeast, insect, or, in particular, a mammalian cell which comprises a DNA molecule encoding a human Y4 receptor and the regulatory elements necessary for expression of the DNA in the bacterial, yeast, insect, or mammalian cell operatively linked to the DNA encoding a human Y4 receptor as to permit expression thereof. Some plasmids adapted for expression in a mammalian cell are pSVL (available from Pharmacia, Piscataway, N.J.) and pcEXV-3 (Miller J. and Germain R. N., J. Exp. Med. 164:1478 (1986)). A specific example of such plasmid is a plasmid adapted for expression in a mammalian cell comprising cDNA having coding sequences substantially the same as the coding sequence shown in FIGS. 1A–1E and the regulatory elements necessary for expression of the DNA in the mammalian cell which is designated pcEXV-Y4 and deposited under ATCC Accession No. 75631. Those skilled in the art will readily appreciate that numerous plasmids adapted for expression in a mammalian cell which comprise DNA of encoding human Y4 receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposit discussed supra, and the other deposits discussed herein, were made pursuant to, and in satisfaction of, the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a human Y4 receptor, such as a mammalian cell comprising a plasmid adapted for expression in a mammalian cell, which comprises a DNA molecule encoding a human Y4 receptor, the protein encoded thereby is expressed on the cell surface, and the regulatory elements necessary for expression of the DNA in the mammalian cell operatively linked to the DNA encoding a human Y4 receptor as to permit expression thereof. Numerous mammalian cells may be used as hosts, including, for example, the mouse fibroblast cell NIH3T3, CHO cells, HeLa cells, L-M(TK-) cells, Y1 cells, etc. Expression plasmids such as that described supra may be used to transfect mammalian cells by methods well known in the art such as calcium phosphate precipitation, or DNA encoding these Y4 receptors may be otherwise introduced into mammalian cells, e.g., by microinjection, to obtain mammalian cells which comprise DNA, e.g., cDNA or a plasmid, encoding either human Y4 receptor.

This invention provides a method for determining whether a ligand not known to be capable of binding to a human Y4 receptor can bind to a human Y4 receptor which comprises contacting a mammalian cell comprising a DNA molecule encoding a human Y4 receptor, the protein encoded thereby is expressed on the cell surface, with the ligand under conditions permitting binding of ligands known to bind to the Y4 receptor, detecting the presence of any of the ligand bound to the Y4 receptor, and thereby determining whether the ligand binds to the Y4 receptor. This invention also provides a method for determining whether a ligand not known to be capable of binding to the human Y4 receptor can act as a human Y4 receptor agonist. As used herein, the term "agonist" means any ligand capable of increasing human Y4 receptor normal functional activity. This comprises contacting a mammalian cell comprising an isolated DNA molecule which encodes a human Y4 receptor with the ligand under conditions permitting the activation of a functional response, detected by means of a bioassay from the mammalian cell such as a second messenger response, and detecting an increase in Y4 receptor activity, and thereby determining which ligands act as a human Y4 receptor agonist. This invention also provides a method for determining whether a ligand not known to be capable of binding to the human Y4 receptor can act as a human Y4 receptor antagonist. As used herein, the term "antagonist" means any ligand capable of inhibiting Y4 receptor normal functional activity. This comprises contacting a mammalian cell comprising an isolated DNA molecule which encodes a human Y4 receptor with the ligand and a known human Y4 receptor agonist such as PP, under conditions permitting the activation of a functional response, detected by means of a bioassay from the mammalian cell, such as a second messenger response, a decrease in human Y4 receptor activity, and thereby determining which ligands act as human Y4 receptor antagonists. The DNA in the mammalian cell may have a coding sequence substantially the same as the coding sequence shown in FIG. 1. Preferably, the mammalian cell is nonneuronal in origin. An example of a nonneuronal mammalian cell is a COS-7 cell. Other examples of a non-neuronal mammalian cells that can be used for functional assays with human receptors are Y1 murine adrenal and L-M(TK-) cells. The preferred method for determining whether a ligand is capable of binding to the human Y4 receptor comprises contacting a transfected nonneuronal mammalian cell (i.e. a cell that does not naturally express any type of NPY, PP, or PYY receptor, thus will only express such a receptor if it is transfected into the cell) expressing a Y4 receptor on its surface, or contacting a membrane preparation derived from such a transfected cell, with the ligand under conditions which are known to prevail, and thus to be associated with, in vivo binding of the ligands to a Y4 receptor, detecting the presence of any of the ligand being tested bound to the Y4 receptor on the surface of the cell, and thereby determining whether the ligand binds to, activates or inhibits the activation of the Y4 receptor. This response system is obtained by transfection of isolated DNA into a suitable host cell containing the desired second messenger system such as phosphoinositide hydrolysis, adenylate cyclase, guanylate cyclase or ion channels. Such a host system is isolated from pre-existing cell lines, or can be generated by inserting appropriate components of second messenger systems into existing cell lines. Such a transfection system provides a complete response system for investigation or assay of the activity of human Y4 receptors with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of second messenger systems or their sequelae in transfection systems act as assays for binding affinity and efficacy in the activation of receptor function. A transfection system constitutes a "drug discovery system" useful for the identification of natural or synthetic compounds with potential for drug development that can be further modified or used directly as therapeutic compounds to activate or inhibit the natural functions of the human Y4 receptor. The transfection system is also useful for determining the affinity and efficacy of known drugs at the human Y4 receptor sites.

This invention also provides a method of screening drugs to identify drugs which specifically interact with, and bind to, the human Y4 receptor on the surface of a cell which comprises contacting a mammalian cell comprising a DNA molecule encoding a human Y4 receptor on the surface of a cell with a plurality of drugs, determining those drugs which bind to the mammalian cell, and thereby identifying drugs which specifically interact with, and bind to, the human Y4 receptor. This invention also provides a method of screening drugs to identify drugs which interact with, and act as human Y4 receptor agonists which comprises contacting the mammalian cell comprising an isolated DNA molecule encoding and expressing a human Y4 receptor with a plurality of drugs under conditions permitting the activation of a functional human Y4 receptor response, determining those drugs which activate the human Y4 receptor in the mammalian cell using a bioassay, such as a second messenger assays, and thereby identifying drugs which specifically interact with, and act as a human Y4 receptor agonist. This invention also provides a method of screening drugs to identify drugs which interact with and act as a human Y4 receptor antagonist which comprises contacting the mammalian cell comprising an isolated DNA molecule encoding and expressing a human Y4 receptor with a plurality of drugs in the presence of a known Y4 receptor agonist such as PP under conditions permitting the activation of a functional human Y4 receptor response, determining those drugs which inhibit the human Y4 receptor in the mammalian cell using a bioassay, such as a second messenger assays, and thereby identifying drugs which specifically interact with, and act as a human Y4 receptor antagonist. The DNA in the cell may have a coding sequence substantially the same as the coding sequence shown in FIGS. 1A–1E. Preferably, the mammalian cell is nonneuronal in origin. An example of a nonneuronal mammalian cell is an COS-7 cell. Other examples of a nonneuronal mammalian cell to be used for functional assays are Y1 murine adrenal and L-M(TK-) cells. Drug candidates are identified by choosing chemical compounds which bind with high affinity to the expressed Y4 receptor protein in transfected cells, using radioligand binding methods well known in the art, examples of which are shown in the binding assays described herein. Drug candidates are also screened for selectivity by identifying compounds which bind with high affinity to the human Y4 receptor but do not bind with high affinity to any other NPY receptor subtype or to any other known receptor site. Because selective, high affinity compounds interact primarily with the target Y4 receptor site after administration to the patient, the chances of producing a drug with unwanted side effects are minimized by this approach. This invention provides a pharmaceutical composition comprising a drug identified by the method described above and a pharmaceutically acceptable carrier. As used herein, the term „pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bioavailable following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bioavailable, in an appropriate solid or solution formulation, to gain the desired therapeutic benefit.

This invention provides a nucleic acid probe comprising a nucleic acid molecule of at least 15 nucleotides capable of specifically hybridizing with a unique sequence included within the sequence of a nucleic acid molecule encoding a human Y4 receptor, for example with a coding sequence included within the sequence shown in FIGS. 1A–1E. As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the human Y4 receptor. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding human Y4 receptors is useful as a diagnostic test for any disease process in which levels of expression of the corresponding Y4 receptor is altered. DNA probe molecules are produced by insertion of a DNA molecule which encodes human Y4 receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. An example of such DNA molecule is shown in FIGS. 1A–1E. The probes are useful for 'in situ' hybridization or in order to locate tissues which express this gens family, or for other hybridization assays for the presence of these genes or their mRNA in various biological tissues. In addition, synthesized oligonucleotides (produced by a DNA synthesizer) complementary to the sequence of a DNA molecule which encodes human Y4 receptor of are useful as probes for these genes, for their associated mRNA, or for the isolation of related genes by homology screening of genomic or cDNA libraries, or by the use of amplification techniques such as the Polymerase Chain Reaction. Synthesized oligonucleotides as described may also be used to determine the cellular localization of the mRNA produced by the Y4 gene by in situ hybridization.

This invention also provides a method of detecting expression of a Y4 receptor on the surface of a cell by detecting the presence of mRNA coding for a Y4 receptor which comprises obtaining total mRNA from the cell using methods well known in the art and contacting the mRNA so obtained with a nucleic acid probe comprising a nucleic acid molecule of at least 15 nucleotides capable of specifically hybridizing with a sequence included within the sequence of a nucleic acid molecule encoding a human Y4 receptor under hybridizing conditions, detecting the presence of mRNA hybridized to the probe, and thereby detecting the expression of the Y4 receptor by the cell. Hybridization of probes to target nucleic acid molecules such as mRNA molecules employs techniques well known in the art. In one possible means of performing this method, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of specifically hybridizing with any sequences of an mRNA molecule which encodes a human Y4 receptor so as to prevent translation of the mRNA molecule. The antisense oligonucleotide may have a sequence capable of specifically hybridizing with any sequences of the cDNA molecule whose sequence is shown in FIGS. 1A–1E. A particular example of an antisense oligonucleotide is an antisense oligonucleotide comprising chemical analogues of nucleotides.

This invention also provides a pharmaceutical composition comprising an amount of the oligonucleotide described above effective to reduce expression of a human Y4 receptor by passing through a cell membrane and specifically hybridizing with mRNA encoding a human Y4 receptor in the cell so as to prevent its translation and a pharmaceutically acceptable hydrophobic carrier capable of passing through a cell membrane. The oligonucleotide may be coupled to a substance which inactivates mRNA, such as a ribozyme. The pharmaceutically acceptable hydrophobic carrier capable of passing through cell membranes may also comprise a structure which binds to a receptor specific for a selected cell type and is thereby taken up by cells of the selected cell type. The structure may be part of a protein known to bind a cell-type specific receptor, for example an insulin molecule, which would target pancreatic cells. DNA molecules having coding sequences substantially the same as the coding sequence shown in FIGS. 1A–1E may be used as the oligonucleotides of the pharmaceutical composition.

This invention also provides a method of treating abnormalities which are alleviated by reduction of expression of a Y4 receptor which comprises administering to a subject an amount of the pharmaceutical composition described above effective to reduce expression of the Y4 receptor by the subject. This invention further provides a method of treating an abnormal condition related to Y4 receptor activity which comprises administering to a subject an amount of the pharmaceutical composition described above effective to reduce expression of the Y4 receptor by the subject. Several examples of such abnormal conditions are amnesia, depression, anxiety, epilepsy, pain, depression, hypertension, and sleep and eating disorders.

Antisense oligonucleotide drugs inhibit translation of mRNA encoding these receptors. Synthetic oligonucleotides, or other antisense chemical structures are designed to bind to mRNA encoding the Y4 receptor and inhibit translation of mRNA and are useful as drugs to inhibit expression of Y4 receptor genes in patients. This invention provides a means to therapeutically alter levels of expression of human Y4 receptors by the use of a synthetic antisense oligonucleotide drug (SAOD) which inhibits translation of mRNA encoding these receptors. Synthetic oligonucleotides, or other antisense chemical structures designed to recognize and selectively bind to mRNA, are constructed to be complementary to portions of the nucleotide sequences shown in FIGS. 1A-1E of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g. by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which binds and takes up the SAOD only within certain selected cell populations. For example, the SAOD may be designed to bind to a receptor found only in a certain cell type, as discussed above. The SAOD is also designed to recognize and selectively bind to the target mRNA sequence, which may correspond to a sequence contained within the sequence shown in FIGS. 1A-1E by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci. 10,435 (1989); H. M. Weintraub, Sci. Am. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce receptor expression in particular target cells of a patient, in any clinical condition which may benefit from reduced expression of Y4 receptors.

This invention provides an antibody directed to the human Y4 receptor, for example a monoclonal antibody directed to an epitope of a human Y4 receptor present on the surface of a cell and having an amino acid sequence substantially the same as an amino acid sequence for a cell surface epitope of the human Y4 receptor included in the amino acid sequence shown in FIGS. 1A-1E (Seq. I.D. No. 2). Amino acid sequences may be analyzed by methods well known in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1A-1E will probably bind to a surface epitope of a human Y4 receptor, as described. Antibodies directed to human Y4 receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as COS-7 cells or L-M(TK-) cells comprising DNA encoding the human Y4 receptor and thereby expressing the human Y4 receptor may be used as immunogens to raise such an antibody. Alternatively, synthetic peptides may be prepared using commercially available machines and the amino acid sequence shown in FIGS. 1A-1E (Seq. I.D. No. 2). As a still further alternative, DNA, such as a cDNA or a fragment thereof, may be cloned and expressed and the resulting polypeptide recovered and used as an immunogen. These antibodies are useful to detect the presence of human Y4 receptors encoded by the isolated DNA, or to inhibit the function of the receptors in living animals, in humans, or in biological tissues or fluids isolated from animals or humans.

This invention provides a pharmaceutical composition which comprises an amount of an antibody directed to the human Y4 receptor effective to block binding of naturally occurring ligands to the Y4 receptor, and a pharmaceutically acceptable carrier. A monoclonal antibody directed to an epitope of a human Y4 receptor present on the surface of a cell and having an amino acid sequence substantially the same as an amino acid sequence for a cell surface epitope of the human Y4 receptor included in the amino acid sequence shown in FIGS. 1A-1E is useful for this purpose.

This invention also provides a method of treating abnormalities which are alleviated by reduction of expression of a human Y4 receptor which comprises administering to a subject an amount of the pharmaceutical composition described above effective to block binding of naturally occurring ligands to the Y4 receptor and thereby alleviate abnormalities resulting from overexpression of a human Y4 receptor. Binding of the antibody to the receptor prevents the receptor from functioning, thereby neutralizing the effects of overexpression. The monoclonal antibodies described above are both useful for this purpose. This invention additionally provides a method of treating an abnormal condition related to an excess of Y4 receptor activity which comprises administering to a subject an amount of the pharmaceutical composition described above effective to block binding of naturally occurring ligands to the Y4 receptor and thereby alleviate the abnormal condition. Some examples of abnormal conditions are amnesia, depression, anxiety, epilepsy, pain, depression, hypertension, and sleep and eating disorders.

This invention provides a method of detecting the presence of a Y4 receptor on the surface of a cell which comprises contacting the cell with an antibody directed to the human Y4 receptor, under conditions permitting binding of the antibody to the receptor, detecting the presence of the antibody bound to the cell, and thereby the presence of the human Y4 receptor on the surface of the cell. Such a method is useful for determining whether a given cell is defective in expression of Y4 receptors on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a human Y4 receptor. This invention also provides a transgenic nonhuman mammal comprising a homologous recombination knockout of the native Y4 receptor. This invention also provides a transgenic nonhuman mammal whose genome comprises antisense DNA complementary to DNA encoding a human Y4 receptor so placed as to be transcribed into antisense mRNA which is complementary to mRNA encoding a Y4 receptor and which hybridizes to mRNA encoding a Y4 receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequence shown in FIGS. 1A–1E. An example of a transgenic animal is a transgenic mouse. Examples of tissue specificity-determining regions are the metallothione in promotor (Low, M. J., Lechan, R. M., Hammer, R. E. et al. Science 231:1002–1004 (1986)) and the L7 promotor (Oberdick, J., Smeyne, R. J., Mann, J. R., Jackson, S. and Morgan, J. I. Science 248:223–226 (1990)). Animal model systems which elucidate the physiological and behavioral roles of human Y4 receptors are produced by creating transgenic animals in which the expression of a Y4 receptor is either increased or decreased, or the amino acid sequence of the expressed Y4 receptor protein is altered, by a variety of techniques. Examples of these techniques include: 1) Insertion of normal or mutant versions of DNA encoding a human Y4 receptor or homologous animal versions of these genes, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)). 2) Homologous recombination (Capecchi M. R. Science 244:1288–1292 (1989); Zimmer, A. and Gruss, P. Nature 338:150–153 (1989)) of mutant or normal, human or animal versions of these genes with the native gene locus in transgenic animals to alter the regulation of expression or the structure of these Y4 receptors. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a human Y4 receptor is purified from a vector (such as plasmid pcEXV-Y4 described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit the receptor, the transgenic animal model systems described above are useful for testing the biological activity of drugs directed against these Y4 receptors even before such drugs become available. These animal model systems are useful for predicting or evaluating possible therapeutic applications of drugs which activate or inhibit these human Y4 receptors by inducing or inhibiting expression of the native or trans-gene and thus increasing or decreasing expression of normal or mutant human Y4 receptors in the living animal. Thus, a model system is produced in which the biological activity of drugs directed against these Y4 receptors are evaluated before such drugs become available. The transgenic animals which over or under produce the human Y4 receptor indicate by their physiological state whether over or under production of the human Y4 receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to underexpression. Therefore, an animal which underexpresses receptor is useful as a test system to investigate whether the actions of such drugs which result in under expression are in fact therapeutic. Another use is that if overexpression is found to lead to abnormalities, then a drug which downregulates or acts as an antagonist to Y4 receptor is indicated as worth developing, and if a promising therapeutic application is uncovered by these animal model systems, activation or inhibition of the Y4 receptor is achieved therapeutically either by producing agonist or antagonist drugs directed against these Y4 receptors or by any method which increases or decreases the expression of these Y4 receptors in man.

This invention provides a method of determining the physiological effects of expressing varying levels of human Y4 receptors which comprises producing a transgenic nonhuman animal whose levels of human Y4 receptor expression are varied by use of an inducible promoter which regulates human Y4 receptor expression. This invention also provides a method of determining the physiological effects of expressing varying levels of human Y4 receptors which comprises producing a panel of transgenic nonhuman animals each expressing a different amount of human Y4 receptor. Such animals may be produced by introducing different amounts of DNA encoding a human Y4 receptor into the oocytes from which the transgenic animals are developed.

This invention also provides a method for identifying a substance capable of alleviating abnormalities resulting from overexpression of a human Y4 receptor comprising administering the substance to a transgenic nonhuman mammal expressing at least one artificially introduced DNA molecule encoding a human Y4 receptor and determining whether the substance alleviates the physical and behavioral abnormalities displayed by the transgenic nonhuman mammal as a result of overexpression of a human Y4 receptor. As used herein, the term "substance" means a compound or composition which may be natural, synthetic, or a product derived from screening. Examples of DNA molecules are DNA or cDNA molecules having a coding sequence substantially the same as the coding sequence shown in FIGS. 1A–1E.

This invention provides a pharmaceutical composition comprising an amount of the substance described supra effective to alleviate the abnormalities resulting from overexpression of Y4 receptor and a pharmaceutically acceptable carrier.

This invention further provides a method for treating the abnormalities resulting from overexpression of a human Y4 receptor which comprises administering to a subject an amount of the pharmaceutical composition described above effective to alleviate the abnormalities resulting from overexpression of a human Y4 receptor.

This invention provides a method for identifying a substance capable of alleviating the abnormalities resulting from underexpression of a human Y4 receptor comprising administering the substance to the transgenic nonhuman mammal described above which underexpresses human Y4 receptor and determining whether the substance alleviates the physical and behavioral abnormalities displayed by the transgenic nonhuman mammal as a result of underexpression of a human Y4 receptor.

This invention also provides a pharmaceutical composition comprising an amount of a substance effective to alleviate abnormalities resulting from underexpression of Y4 receptor and a pharmaceutically acceptable carrier.

This invention further provides a method for treating the abnormalities resulting from underexpression of a human Y4 receptor which comprises administering to a subject an amount of the pharmaceutical composition described above effective to alleviate the abnormalities resulting from underexpression of a human Y4 receptor.

This invention provides a method for diagnosing a predisposition to a disorder associated with the expression of a specific human Y4 receptor allele which comprises: a) obtaining DNA of subjects suffering from the disorder; b) performing a restriction digest of the DNA with a panel of restriction enzymes; c. electrophoretically separating the resulting DNA fragments on a sizing gel; d) contacting the resulting gel with a nucleic acid probe capable of specifically hybridizing to DNA encoding a human Y4 receptor and labelled with a detectable marker; e) detecting labelled bands which have hybridized to the DNA encoding a human Y4 receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human Y4 receptor allele.

This invention provides a method of preparing the isolated Y4 receptor which comprises inducing cells to express Y4 receptor, recovering the receptor from the resulting cells, and purifying the receptor so recovered. An example of an isolated Y4 receptor is an isolated protein having substantially the same amino acid sequence as the amino acid sequence shown in FIGS. 1A–1E. For example, cells can be induced to express receptors by exposure to substances such as hormones. The cells can then be homogenized and the receptor isolated from the homogenate using an affinity column comprising, for example, PP or another substance which is known to bind to the receptor. The resulting fractions can then be purified by contacting them with an ion exchange column, and determining which fraction contains receptor activity or binds anti-receptor antibodies.

This invention provides a method of preparing the isolated Y4 receptor which comprises inserting nucleic acid encoding Y4 receptor in a suitable vector, inserting the resulting vector in a suitable host cell, recovering the receptor produced by the resulting cell, and purifying the receptor so recovered. An example of an isolated Y4 receptor is an isolated protein having substantially the same amino acid sequence as the amino acid sequence shown in FIGS. 1A–1E. This method for preparing Y4 receptor uses recombinant DNA technology methods well known in the art. For example, isolated nucleic acid encoding Y4 receptor is inserted in a suitable vector, such as an expression vector. A suitable host cell, such as a bacterial cell, or a eukaryotic cell such as a yeast cell, is transfected with the vector. Y4 receptor is isolated from the culture medium by affinity purification or by chromatography or by other methods well known in the art.

This invention provides an antisense oligonucleotide having a sequence capable of binding specifically with any sequences of an mRNA molecule which encodes a receptor so as to prevent translation of the mRNA molecule.

This invention also provides a transgenic nonhuman mammal expressing DNA encoding a receptor.

This invention further provides a transgenic nonhuman mammal comprising a homologous recombination knockout of the native Y4 receptor.

This invention provides a method of determining the physiological effects of expressing varying levels of a receptor which comprises producing a transgenic nonhuman animal whose levels of receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding the receptor with the ligand under conditions permitting binding of ligands known to bind to a receptor, detecting the presence of any of the ligand bound to the receptor, and thereby determining whether the ligand binds to the receptor.

This invention identifies for the first time a new receptor protein, its amino acid sequence, and its human gene. Furthermore, this invention describes a previously unrecognized group of receptors within the definition of a Y4 receptor. The information and experimental tools provided by this discovery are useful to generate new therapeutic agents, and new therapeutic or diagnostic assays for this new receptor protein, its associated mRNA molecule or its associated genomic DNA. The information and experimental tools provided by this discovery will be useful to generate new therapeutic agents, and new therapeutic or diagnostic assays for this new receptor protein, its associated mRNA molecule, or its associated genomic DNA.

Specifically, this invention relates to the first isolation of a human genomic clone encoding a Y4 receptor. A new human gene for the receptor identified herein as Y4 has been identified and characterized. In addition, the human-Y4 receptor has been expressed in COS-7 cells. The pharmacological binding properties of the protein encoded have been determined, and these binding properties classify this protein as a novel human NPY/PYY/PP receptor which we designate as a human Y4 receptor. Mammalian cell lines expressing this human Y4 receptor at the cell surface have been constructed, thus establishing the first well-defined, cultured cell lines with which to study this Y4 receptor.

This invention will be better understood by reference to the Experimental Details which follow, but those skilled in the art will readily appreciate that the specific experiments detailed are only illustrative of the invention as described more fully in the claims which follow thereafter.

Experimental Details

Cloning and Sequencing

A human placenta genomic library in λ dash II (≈1.5×10$^6$ total recombinants; Stratagene, LaJolla, CA) was screened using overlapping transmembrane (TM) oligonucleotide probes (TM 1, 2, 3, 5 and 7) derived from the rat Y1 neuropeptide receptor gene (Eva, C. et al., 1990; GenBank accession No. Z11504). Overlapping oligomers (TM1: nts. 198–251, (+) strand/5'-TTGCTTATGGGGCTGTGATTAT-TCTTGGGGTCTCTGGAAACCTGG-3' (Sequence I.D. No. 3 ) and (−) strand/5 '-TAGGATGATTATGATCAATGC-CAGGTTTCCAGAGACCCCAAGAAT-3' (Sequence I.D. No. 4 ); TM2: nts. 269–328, (+) strand/5'-AAAGAGAT-GAGGAATGTCACCAACATTCTGATCGT GAAC-CTCTCC-3' (Sequence I.D. No. 5) and (−)strand/5' -CAG-CAAGTCTGAGAAGGAGAGGTTCACGATCAGAATG TTGGTGAC-3' (Sequence I.D. No. 6); TM3: nts. 401–478, (+)strand/5'     -TGCAAACTGAATCCTTTTGTGCAAT-GCGTCTCCATTACAGTATCCATTTTCTCT-         3' (Sequence I.D. No. 7) and (−) strand/5'-ACGTTCCACAGC GATGAGAACCAGAGAGAAAATGGATACT-GTAATGGAGACGCA-3' ( Sequence I.D. No. 8);TM5: nts. 716–778, (+)strand/5' -CTGCAGTATTTTGGCCCACTCT-GTTTCATATTCATATGCTAC-3' ( Sequence I.D. No. 9) and (−)strand/5' -CAAGCGAATGTATATCTTGAAGTAG-CATATGAATATGAAACA-3' ( Sequence I.D. No. 10); TM7: nts. 971–1045, (+)strand/5'-CTGCTCTGCCACCT-CACGGCCATGATCTCCACCTGCGTCAACC CCATC-3' (Sequence I.D. No. 11) and (−) strand/5'-GAAATTTTTGT-TCAGGAATCCATAAAAGATGGGGTTGA CGCAG-GTGGA-3' (Sequence I.D. No. 12); GenBank accession No. Z11504) were labeled with [$^{32}$P]dATP and [$^{32}$P]dCTP by synthesis with the large fragment of DNA polymerase. Hybridization was performed at low stringency conditions: 40° C. in a solution containing 25.0% formamide, 5×SSC (1×SSC is 0.15 M sodium chloride, 0.015 M sodium citrate), 1× Denhardt's solution (0.02% polyvinylpyrrolindone, 0.02% Ficoll, 0.02% bovine serum albumin), and 25 μg/μl sonicated salmon sperm DNA. The filters were washed at 40° C. in 0.1×SSC containing 0.1% sodium dodecyl sulfate and exposed at −70° C. to Kodak XAR film in the presence of an intensifying screen. Lambda phage clones hybridizing with the probes were plaque purified and DNA was prepared for Southern blot analysis (Southern, 1975; Sambrook et al., 1989). For subcloning and further Southern blot analysis, DNA was cloned into pUC18 (Pharmacia, Piscataway, N.J.). Nucleotide sequence analysis was accomplished by the Sanger dideoxy nucleotide chain termination method (Sanger et al., 1977) on denatured double-stranded plasmid templates, using Sequenase (U.S. Biochemical Corp., Cleveland, Ohio).

Expression

The entire coding region of hp25a (1127 bp), including 680 bp of 5' untranslated (5' UT) and 205 bp of 3' untranslated sequence (3' UT), was cloned into the BamHI and EcoRI sites of the polylinker-modified eukaryotic expression vector pCEXV-3 (Miller et al., 1986), called EXJ.HR (J.B., unpublished data). Monkey kidney cells (Cos-7) were transiently transfected with plasmid hp25a/EXJ (expression vector containing the hp25a receptor gene) using DEAE dextran methodology (reagents obtained from Specialty Media, Lavellette, N.J.).

Cell culture

COS-7 cells were grown on 150 mm plates (Corning) in D-MEM with supplements (Dulbecco's Modified Eagle Medium with 10% bovine calf serum, 2 mM glutamine, 100 units/ml penicillin/80 units/ml streptomycin) at 37 ° C., 5% CO$_2$. Stock plates of COS-7 cells were trypsinized and split 1:6 every 3–4 days. SK-N-Be(2) human neuroblastoma cells were grown similarly in 225 cm$^2$ flasks (Co-star) using 50% Eagle's Modified Essential Media, 50% Ham's Nutrient Mixture F- 12, 15% fetal bovine serum, 2 mM glutamine, 100 units/ml penicillin/80 units/ml streptomycin, and 1% nonessential amino acids. Stock flasks of SK-N-Be(2) cells were trypsinized and split 1:10 every 7 days. Cell culture media and supplements were from Specialty Media (Lavallette, N.J.). Cell culture plates (150 mm) were from Corning (Corning, N.Y.). Cell culture flasks (225 cm$^2$) and polypropylene microtiter plates were from Co-star (Cambridge, Mass.).

Membrane Harvest

Membranes were harvested from COS-7 cells 48 hours after transfection and from SK-N-Be(2) seven days after splitting. Adherent cells were washed twice in ice-cold phosphate buffered saline (138 mM NaCl, 8.1 mMNa$_2$HPOhd 4, 2.5 mM KCl, 1.2 mM KH$_2$PO$_4$, 0.9 mM CaCl$_2$, 0.5 mMMgCl$_2$, pH 7.4) and lysed by sonication in ice-cold hypotonic buffer (20 mM Tris-HCl, 5 mM EDTA, pH 7.7). Large particles and debris were cleared by low speed centrifugation (200×g, 10 min, 4 °C.). Membranes were collected from the supernatant fraction by high speed centrifugation (32,000×g, 18 min, 4° C.), washed with ice-cold hypotonic buffer, and collected again by high speed centrifugation (32,000×g, 18 min, 4 °C.). The final membrane pellet was resuspended by sonication into a small volume (−500 µl) of ice-cold binding buffer (10 mM NaCl, 20 mM HEPES, 0.22 mM $KH_2PO_4$, 1.26 mM$CaCl_2$, 0.81 mM$MgSO_4$, pH 7.4). Protein concentration was measured by the Bradford method (Bradford, 1976) using Bio-Rad Reagent, with bovine serum albumin as a standard.

Radioligand Binding to Membrane Suspensions

Membrane suspensions were diluted in binding buffer supplemented with 0.1% bovine serum albumin and 0.1% bacitracin to yield an optimal membrane protein concentration: ~0.02 mg/ml for human Y1 receptors, ~0.015 mg/ml for hp25a receptors, and ~0.25 mg/ml for SK-N-Be(2). (Under these conditions, $^{125}$I-PYY bound by membranes in the assay was less than 10% of $^{125}$I-PYY delivered to the sample.) $^{125}$I-PYY and non-labeled peptide competitors were also diluted to desired concentrations in supplemented binding buffer. Individual samples were then prepared in 96-well polypropylene microtiter plates by mixing membrane suspensions (200 ul), $^{125}$I-PYY (25 ul), and non-labeled peptides or supplemented binding buffer (25 ul). Samples were incubated in a 30 °C. water bath with constant shaking for 120 min. Incubations were terminated by filtration over Whatman GF/C filters (pre-coated with 0.5% polyethyleneimine and air-dried before use). Filter-trapped membranes were counted for $^{125}$I in a gamma counter. Non-specific binding was defined by 100 nM human PP for hp25a receptors and by 100 nM NPY for Y1 and SK-N-Be(2) receptors. Specific binding in time course and competition studies was typically 80%; most nonspecific binding was associated with the filter. Binding data were analyzed using nonlinear regression and statistical techniques available in the GraphPAD InPlot package (San Diego, Calif.). Porcine $^{125}$I-PYY was from New England Nuclear (Boston, Mass.). NPY and related peptide analogs were from either Bachem California (Torrance, Calif.) or Peninsula (Belmont, Calif.). Whatman GF/C filters were from Brandel (Gaithersburg, Md.). Bio-Rad Reagent was from Bio-Rad (Hercules, Calif.). Bovine serum albumin and bacitracin were from Sigma (St. Louis. Mo.). All other materials were reagent grade.

Results

We screened a human genomic placenta library, under reduced stringency conditions, with oligonucleotide probes directed to the first, second, third, fifth, and seventh transmembrane regions of the rat Y1 neuropeptide receptor gene (Eva, C. et al., 1990; GenBank accession No. Z11504). Positively-hybridizing clones (≈100–150) were isolated, plaque-purified and characterized by Southern blot analysis and sequencing. One clone, hp25a, contained a 1.3 kb PstI fragment which hybridized with the rat Y1-derived oligonucleotide probes and was subsequently subcloned into a pUC vector. DNA sequence analysis indicated greatest homology to the rat and human Y1 receptor genes. This clone was a partial intronless gene fragment, encoding part of the third intracellular loop through the carboxyl terminus, including a termination codon.

In order to obtain a full-length clone, a 2.0 kb BamHI/EcoRI hybridizing fragment, containing the entire coding region, which was intronless, was subcloned into an expression vector and sequenced. The genomic full-length construct in the expression vector (called hp25a/EXJ) contains an open reading frame of 1127 bp, with 680 bp of the predicted 5' UT and 205 bp of predicted 3' UT sequence, and encodes a protein of 375 aa in length, with a relative molecular mass of ≈41,000 daltons. Hydropathy analysis of the protein is consistent with a putative topography of seven transmembrane domains, indicative of the G protein-coupled receptor family.

Initial sequence analysis revealed that clone hp25a/EXJ contained several conserved structural features/residues found among the members of the neuropeptide receptor family, including two glycines and asparagine in TM1 (positions 55, 58 and 59, respectively, in FIG. 2A–2C), an asparagine, leucine and aspartic acid in TM2 (positions 82, 83, and 87, respectively, in FIG. 2A–2C), a serine and leucine in TM3 (positions 128 and 132, respectively, in FIGS. 2A–2C), a tryptophan and proline in TM4 (positions 164 and 173, respectively, in FIGS. 2A–2C), a tyrosine and proline in TM5 (positions 223 and 226, respectively, in FIGS. 2A–2C), a phenylalanine, tryptophan, and proline in TM6 (positions 275, 279, and 281, respectively, in FIGS. 2A–2C), and a serine, threonine, asparagine, and proline in TM7 (positions 315, 316, 319, and 320, respectively, in FIGS. 2A–2C). Other features of this human hp25a receptor gene are the presence of three potential sites for N-linked glycosylation in the amino terminus (asparagine residues 2, 19, and 29; FIGS. 1A–1E) and the presence of several serines and threonines in the carboxyl terminus and intracellular loops, which may serve as sites for potential phosphorylation by protein kinases.

A comparison of nucleotide and petide sequences of clone hp25a/EXJ with sequences contained in the Genbank/EMBL databases reveals that the clone is most related to the rat, mouse and human Y1 receptor genes and proteins (see FIGS. 2A–2C). The hp25a clone exhibits 42% overall amino acid identity with the human NPY-1 receptor and 55% identity when comparing only the transmembrane domains between hp25a and Y1. The comparison of the individual amino acid residues in the TM domains between hp25a and Y1 reveal <30%, 57%, 57%, 57%, 52%, 63%, and 71% identity in the corresponding one through seven TM regions, repectively. The hp25a clone hybridized only with the TM7-specific probe from the original set of rat-derived TM probes originally used to screen the library which is consistant with the hp25a clone sharing the highest degree of amino acid identity with the TM7 domain of the rat Y1 receptor.

Figure 3:
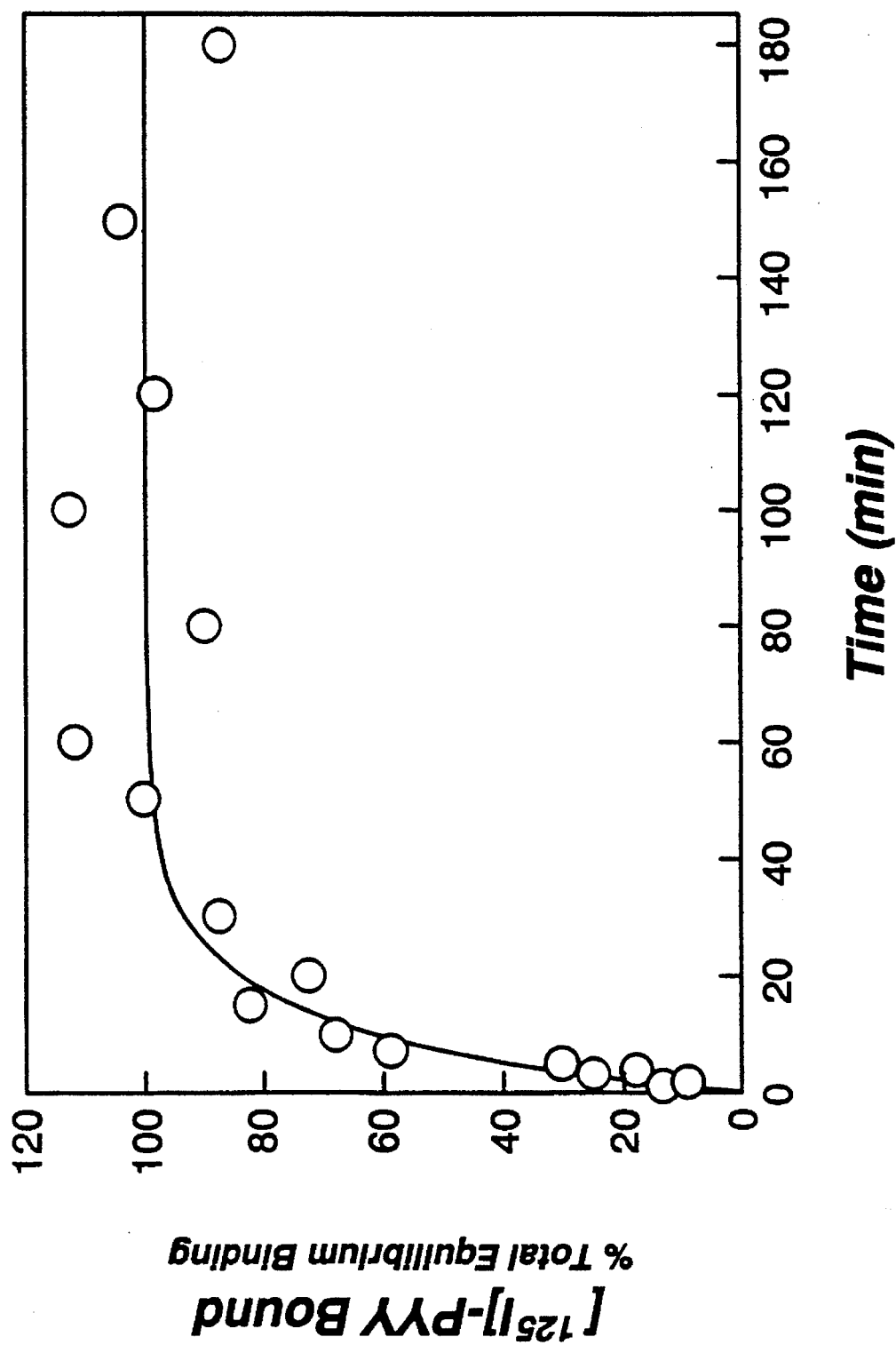

Monkey kidney cells transiently expressing the gene encoding the hp25a receptor were used for pharmacological evaluation. Membranes harvested from transiently transfected Cos-7 cells exhibited high affinity, saturable [$^{125}$I] PYY binding. The time course of specific binding was measured in the presence of 0.06 nM $^{125}$I-PYY (FIG. 3). The association curve was monophasic, with a an observed association rate ($K_{obs}$) of 0.12±0.02 min$^{-1}$ and a $t_{1/2}$ of 6 min; equilibrium binding was 95% complete within 26 min and 100% complete within 50 min (n=3). For comparison, we also measured the time course of binding to human Y1 receptors transiently expressed in COS-7 cells. The association curve was monophasic, with a $K_{obs}$ of 0.06± 0.02 min$^{-1}$ and a $t_{1/2}$ of 12 min; equilibrium binding was 95% complete within 51 min and 100% complete within 90 min (n=3) (data not shown). The different patterns of radioligand association for hp25a and human Y1 receptors suggest novel mechanisms of receptor/ligand interaction.

Saturation binding data for $^{125}$I-PYY were fit to a one-site model with an apparent $K_d$ of 0.11±0.01 nM and an apparent $B_{max}$ of 1.42±0.05 pmol/mg membrane protein, corresponding to approximately 1.4×10$^5$ receptors/cell (n=4; FIG. 4). Given that the transfection efficiency was 20–30% (data not shown), the receptor density on transfected cells was probably closer to $7 \times 10^5$/cell. Membranes from mock-transfected cells, when prepared and analyzed in the same way as those from hp25a-transfected cells, displayed no specific binding of $^{125}$I-PYY. We conclude that the $^{125}$I-PYY binding sites observed under the described conditions were derived from the hp25a construct.

Figure 5:
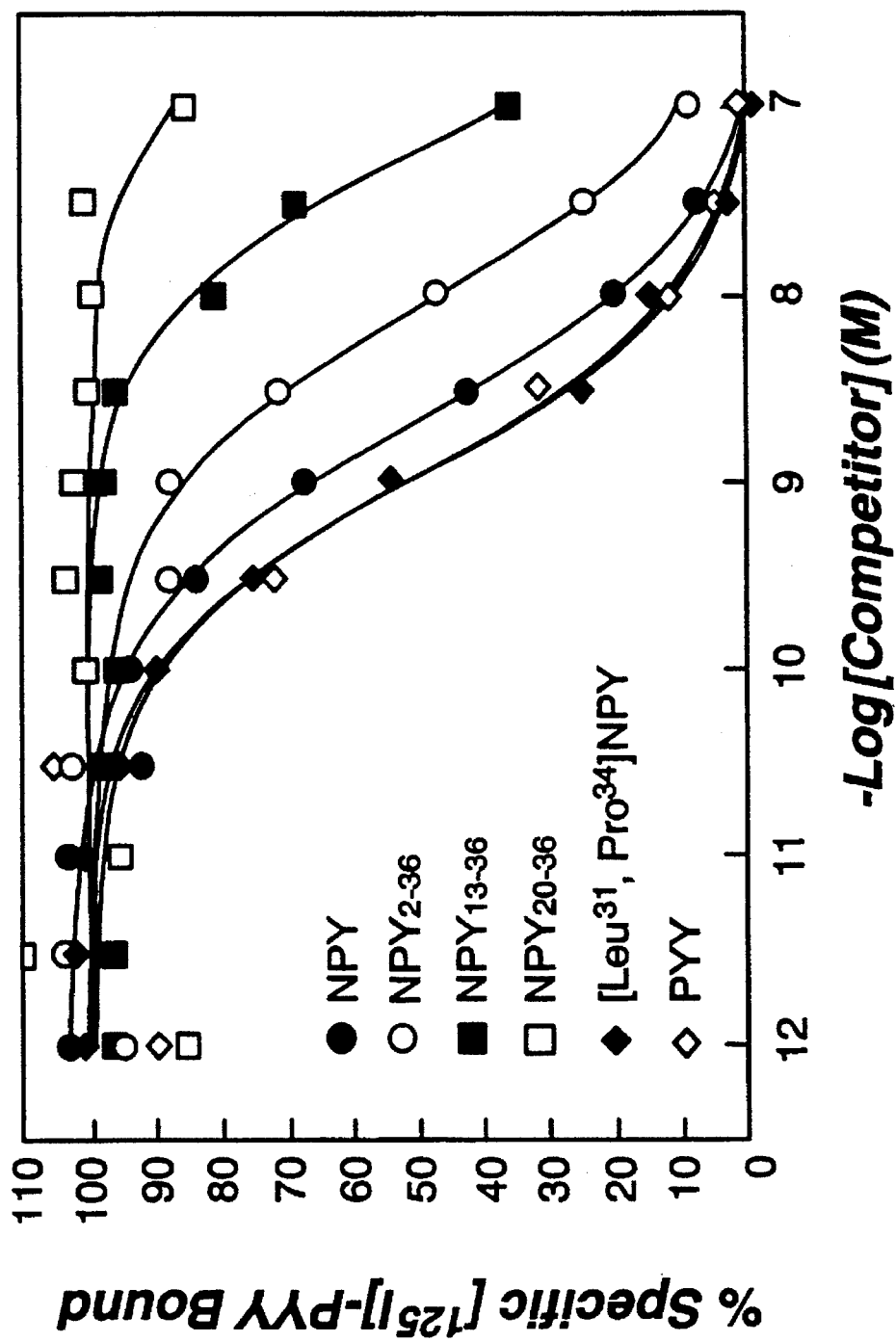

The pharmacological profile of hp25a was defined by membrane binding assays. The receptor was probed for features of all well characterized pancreatic polypeptide family receptors including Y1, Y2, Y3, and PP. The rank order of affinity for several peptide analogs was derived from competitive displacement of $^{125}$I-PYY (FIG. 5 and Table 2). The hp25a receptor was compared with two model systems: 1) the cloned human Y1 receptor (Larhammar et al., 1992; Herzog et al., 1992) transiently expressed in COS-7 cells, and 2) the Y2-like receptor population expressed by human SK-N-Be(2) neuroblastoma cells (Wahlestedt et al., 1991; Dumont et al., 1992). No models for human Y3 and human PP receptors have been described.

PP bound to hp25a with extremely high affinity ($K_i$=0.029 nM) and dramatic selectivity: PP was >6000-fold selective for hp25a over human Y1 receptors ($K_i$=200 nM) and SK-N-Be(2) receptors ($K_i$>300 nM). This profile suggests that hp25a could function selectively as a PP receptor in vivo. The data further indicated, however, that hp25a bound quite well to human NPY ($K_i$ =1.4 nM) and even better to human PYY ($K_i$=0.62 nM). These $K_i$ values, while lower than the $K_i$ for PP, are comparable to the effective concentrations of NPY and PYY from numerous physiological and pharmacological studies (Dumont, 1992). In our investigation, SK-N-Be(2) receptors bound human NPY and human PYY in the same rank order as hp25a but with 5- to 10-fold higher affinity, whereas human Y1 receptors bound human NPY and human PYY in the opposite rank order with 5- to 30fold higher affinity. Hydrolysis of the carboxy terminal amide to free carboxylic acid, as in human NPY free acid, was disruptive for binding to all receptors. A requirement for a carboxy terminal amide appears to be a common structural feature of all pancreatic polypeptide family peptide/receptor interactions.

Fuhlendorff and co-workers replaced Ile$^{31}$ and Gln$^{34}$ in NPY with the corresponding residues from PP to create [Leu$^{31}$,Pro$^{34}$]NPY, which is commonly used to distinguish Y1 from Y2 receptors (Fuhlendorff, 1990). Human [Leu$^{31}$, Pro$^{34}$]NPY displayed >2300-fold selectivity for human Y1 receptors over SK-N-Be(2), but only 5-fold selectivity for human Y1 receptors over hp25a. Human [Leu$^{31}$,Pro$^{34}$]NPY was a better ligand for hp25a ($K_i$=0.60 nM) than was human NPY itself ($K_i$=1.4 nM). This is possibly a reflection of the way in which [Leu$^{31}$,Pro$^{34}$]NPY mimics PP at positions 31 and 34. In contrast, the [Leu$^{31}$,Pro$^{34}$]NPY analog was well tolerated by the human Y1 receptor ($K_i$=0.13 nM), but not preferred over the parent peptide ($K_i$=0.049 nM).

hp25a displayed an intermediate level of sensitivity to N-terminal deletions of NPY and PYY, less so than human Y1 receptors. Removing Tyr$^1$ from porcine NPY resulted in a 29-fold loss in affinity for human Y1 receptors when compared with the full length parent peptide. The same modification decreased affinity 4-fold for hp25a receptors and 3-fold for SK-N-Be(2) receptors. It is interesting in this regard that human PP contains Ala$^1$; the Tyr$^1$ of NPY may not play much of a role in receptor recognition. Truncation to NPY$_{13-36}$ decreased affinity 1000-fold for human Y1 receptors, 33-fold for hp25a, and 4-fold for SK-N-Be(2) receptors. Further truncation to porcine NPY 36 decreased affinity 3500-fold for human Y1 receptors, 120-fold for hp25a, and 11-fold for SK-N-Be(2) receptors. In this regard, the hp25a receptor shares features of both Y1- and Y2-like pharmacology, as would be expected if the N-terminal region of porcine NPY were only moderately involved in receptor recognition.

In summary, hp25a displayed features unique among the neuropeptide receptors, exhibiting a profile which is divergent from its closest relatives, Y1 or Y2, in that it binds optimally to PP rather than to NPY or PYY (see Tables 1 and 2). Unlike the Y1 and Y2 receptor models, hp25a appears to be a reasonable target for all three peptide ligands.

TABLE I

Pharmacologically defined receptors for NPY and related pancreatic polypeptides. Rank orders of affinity are based on published reports of binding and functional data (Wahlestedt et al., 1991; Schwartz et al., 1990; Wahlestedt et al., 1993; Dumont et al., 1992). Missing peptides in the series reflect a lack of published information.

| Receptor | Affinity ($-pK_i$ or $-pEC_{50}$) | | | | | |
|---|---|---|---|---|---|---|
| | 11 to 10 | 10 to 9 | 9 to 8 | 8 to 7 | 7 to 6 | <6 |
| Y1 | NPY<br>PYY<br>[Leu$^{31}$,Pro$^{34}$]NPY | | NPY$_{2-36}$ | NPY$_{13-36}$ | PP | |
| Y2 | | PYY<br>NPY<br>NPY$_{2-36}$ | NPY$_{13-36}$ | | | [Leu$^{31}$,Pro$^{34}$]NPY<br>PP |
| Y3 | | NPY | [Pro$^{34}$]NPY | NPY$_{13-36}$<br>PP | PYY | |
| PP | PP | | [Leu$^{31}$,Pro$^{34}$]NPY | | NPY | |

TABLE 2

Pharmacological profile of the hp25a receptor. Binding data reflect competitive displacement of $^{125}$I-PYY from membranes of COS-7 cells transiently expressing hp25a receptors. Peptides were tested at concentrations ranging from 0.001 nM to 100 nM. IC$_{50}$ values corresponding to 50% displacement were determined by nonlinear regression analysis and converted to $K_i$ values according to the equation, $K_i = IC_{50}/(1 + [L]/K_d)$, where [L] is the $^{125}$I-PYY concentration and $K_d$ equilibrium dissociation constant of $^{125}$I-PYY. The data shown are representative of a least two independent experiments.

| Competitor | Human Y1, $K_i$ (nM) | hp25a, $K_i$ (nM) | SK-N-Be(2), $K_i$ (nM) |
|---|---|---|---|
| human PP | 200 ± 68 | 0.029 ± 0.006 | >300 |

TABLE 2-continued

Pharmacological profile of the hp25a receptor.
Binding data reflect competitive displacement of $^{125}$I-PYY
from membranes of COS-7 cells transiently expressing hp25a
receptors. Peptides were tested at concentrations ranging from
0.001 nM to 100 nM. IC$_{50}$ values corresponding to 50% displacement
were determined by nonlinear regression analysis and
converted to K$_i$ values according to the equation,
K$_i$ = IC$_{50}$/(1 + [L]/K$_d$), where [L] is the $^{125}$I-PYY
concentration and K$_d$ equilibrium dissociation constant of
$^{125}$I-PYY. The data shown are representative of a least two
independent experiments.

| Competitor | Human Y1, K$_i$ (nM) | hp25a, K$_i$ (nM) | SK-N-Be(2), K$_i$ (nM) |
|---|---|---|---|
| human [Leu$^{31}$,Pro$^{34}$]NPY | 0.13 ± 0.02 | 0.60 ± 0.09 | >300 |
| human PPY | 0.085 ± 0.021 | 0.62 ± 0.15 | 0.11 ± 0.02 |
| porcine NPY | 0.049 ± 0.001 | 1.2 ± 0.2 | 0.28 ± 0.04 |
| human NPY | 0.049 ± 0.009 | 1.4 ± 0.1 | 0.13 ± 0.02 |
| porcine NPY$_{2-36}$ | 1.4 ± 0.2 | 4.4 ± 1.3 | 0.41 ± 0.09 |
| porcine NPY$_{13-36}$ | 51 ± 16 | 39 ± 5 | 1.8 ± 0.4 |
| porcine PYY$_{13-36}$ | 32 ± 7 | 47 ± 6 | 0.86 ± 0.14 |
| porcine NPY$_{16-36}$ | 45 ± 4 | 54 ± 2 | 5.0 ± 0.5 |
| porcine NPY$_{18-36}$ | 28 ± 5 | 63 ± 7 | 2.1 ± 0.5 |
| human NPY free acid | >300 | 79 ± 17 | 280 ± 120 |
| porcine NPY$_{20-36}$ | 62 ± 6 | 100 ± 20 | 3.1 ± 0.6 |
| porcine NPY$_{22-36}$ | 170 ± 30 | 140 ± 63 | 3.2 ± 0.6 |
| porcine NPY$_{26-36}$ | >300 | >300 | 70 ± 7 |

Discussion

We have cloned DNA representing a novel human neuropeptide Y/peptide YY/pancreatic polypeptide receptor (Y4) from human genomic DNA. Of all known G protein-coupled receptor sequences (EMBL/Genbank Data Base), the greatest homology was displayed between hp25a and the Y1 receptor genes (mouse—Eva et al., 1992; rat—Eva et al., 1990; and human—Larhammar et al., 1992). Comparison of the human hp25a deduced amino acid sequence with known G protein-coupled receptor sequences indicates the greatest concentration of identical amino acids to be in the transmembrane domains. In these TM regions, the percentage of identity for hp25a clone is 55% compared to human Y1, and less than 35% with other members of the peptide subfamily and other G protein-coupled receptor subfamilies. The alignment of this human hp25a sequence, relative to other G protein-coupled receptors or other members of the neuropeptide subfamily, specifically human Y1, indicates a unique sequence, proving hp25a is a newly characterized receptor. The homology of hp25a to Y1 indicates that it is related to the NPY/YY/PP family of receptors.

Similarly, hp25a exhibits a unique pharmacological profile, suggesting that this receptor can serve as a novel target for the development of subtype selective ligands. The competitive displacement studies indicate that human PP is the preferred ligand for hp25a. The receptor also binds with high affinity to human NPY and human PYY, which share ≧47% amino acid identity with human PP. Affinity is enhanced by modifying NPY to closely resemble PP, as in [Leu$^{31}$,Pro$^{34}$]NPY. Decreased affinity for C-terminal fragments of NPY suggest that both N- and C-terminal regions of NPY contribute to hp25a receptor recognition. hp25a was less sensitive to N-terminal deletion of NPY than was the human Y1 receptor. One may speculate that both Y1 and hp25a share a common mechanism of peptide interaction which has been optimized for either NPY or PP, respectively. As NPY appears to be adequate but not optimal for hp25a receptor recognition, it is conceivable that hp25a binds with higher affinity to N-terminal residues in PP, and would consequently be more sensitive to their removal.

The pharmacological data do not support classification of hp25a as a Y1 receptor, in which case it would display >4000-fold selectivity for binding to human NPY over human PP (Table 2). Neither do the data support classification as a Y2 receptor, in which case it would tolerate N-terminal deletion of NPY but not exchange of Gln$^{34}$ for Pro$^{34}$ (Table 2). Finally, the data fails to support the classification of hp25a as a Y3 receptor, since it would be expected to display greater affinity for NPY than for PP or PYY (Wahlestedt et al., 1991). Therefore, we are designating the hp25a receptor as a Y4 receptor.

The question logically arises as to whether hp25a should be classified as a PP receptor. To our knowledge, no human PP receptor has been described. We must therefore look to the rat PP receptor for comparison. The rat PP receptor bound PP and analogs in the same rank order as hp25a (PP>[Leu$^{31}$,Pro$^{34}$]NPY> NPY) (Schwartz et al., 1990). The rat PP receptor also appeared to bind both N- and C-terminal regions of the peptide ligand (Schwartz et al., 1987). A glaring discrepancy between hp25a and the rat PP receptor is that the latter displayed >10,000-fold selectivity for PP over NPY (Schwartz et al., 1990). Given that the selectivity profile may be a reflection of species variability (the rat PP receptor was characterized with a combination of rat, porcine, and bovine peptide analogs (Schwartz et al., 1987; Schwartz et al., 1990), it is conceivable that hp25a may represent the human analog of the rat PP receptor. We believe that calling hp25a the human PP receptor, however, would be misleading. This is because the relatively compressed window of affinity for PP, PYY, and NPY (0.02 nM≦K$_i$ ≦1.5 nM) makes hp25a a potential target for all three peptide ligands. Future localization experiments may help resolve the relationship between hp25a and the PP receptor.

We propose that hp25a be known as the Y4 receptor. The name is not biased toward any one member of the pancreatic polypeptide family. The "Y" has its roots in the original classification of Y1 and Y2 receptor subtypes (Wahlestedt et al., 1987). The letter reflects the conservation in pancreatic polypeptide family members of the C-terminal tyrosine, described as "Y" in the single letter amino acid code. We note that the cloned human Y1 receptor was introduced by Larhammar and co-workers as a "human neuropeptide Y/peptide YY receptor of the Y1 type", with peptide ligands listed in rank order of affinity (Larhammar et al., 1992). Similarly, hp25a could be described as a human pancreatic polypeptide/peptide YY/neuropeptide Y receptor of the Y4 type.

hp25a is to our knowledge the first "Y type" receptor to be cloned from a subtype family other than Y1. The reported Y3 receptor cloned from bovine brain (Rimland et al., 1991) was later described as having been misidentified (Jazin et al., 1993; Herzog et al., 1993). A Y2-like receptor (PR4) was cloned from drosophila and characterized using mammalian analogs of NPY (Li et al., 1992); however, the classification of this receptor is controversial. The receptor was relatively insensitive to NPY; concentrations ranging from 0.3 to 10 µM were required to elicit calcium mobilization in oocytes injected with PR4 mRNA (Li et al., 1992). The receptor also displayed a rank order of potency for NPY analogs distinct from that observed in mammalian systems (Wahlestedt et al., 1993; Li et al., 1992). Furthermore, an NPY analog has not been isolated from drosophila (Wahlestedt et al., 1993). It is possible that an unidentified ligand in drosophila can activate PR4 more readily than NPY, and as such, the receptor may eventually be reclassified. The cloning and expression of a Y4 (hp25a) receptor represents a major advance in our ability to analyze numerous physiological processes mediated by the pancreatic polypeptide family. Binding sites for PP, PYY, or NPY have a widespread anatomical distribution in brain, spinal cord, sympathetic ganglia, and other peripheral targets such as neuromuscular junction, smooth muscle, stomach chief cells, intestinal enterocytes, kidney proximal tubule, and fat cells (Dumont et al., 1992; Castan et al., 1992). These receptors are therefore in a position to potentially regulate a variety of physiological functions including cognitive enhancement, depression, anxiety, circadian rhythm, EEG synchronization, body temperature, blood pressure, locomotor activity, neuroendocrine release, sexual/reproductive behavior, feeding, sympathetic activation, sensory transmission, gastrointestinal function, intestinal secretion, renal absorption, and cardiovascular function (Wahlestedt et al., 1993). Because pharmacologically defined NPY and PYY receptors have not always been screened with the appropriate analog of PP, it is difficult to say at this time which binding sites or physiological effects could be mediated by the Y4 receptor. The areas in rat where high affinity PP binding has been reported include vas deferens and brainstem nuclei such as the area postrema, interpeduncular nucleus, dorsomedial nucleus, and the nucleus tractus solitarius (Jorgensen et al., 1990; Whitcomb et al., 1990). PP receptors have also been identified on cultured PC-12 cells derived from rat adrenal medulla (Schwartz et al., 1987). The PP receptors in brainstem are accessible to circulating PP, which is released upon vagal stimulation of the pancreas during feeding (Whitcomb et al., 1990). Activation of brainstem PP receptors inhibits vagal tone, thereby forming a negative feedback loop in the digestive process. It is interesting in this regard that PP, along with NPY, and PYY, have all been reported to enhance food intake when injected intracerebroventricularly into rat brain (Clark et al., 1985; Stanley et al., 1985). It is also interesting that a "Y1 variant" receptor proposed to regulate feeding in rats (Stanley et al., 1992) exhibits features of both Y1 and Y2 receptors when probed with analogs of NPY, not unlike Y4. As the "Y1 variant" and other receptors are isolated and more rigorously defined, we can further evaluate the physiological significance of the Y4 receptor. It is tempting to speculate that a Y4-like receptor could be responsible for stimulating food intake in one region of the brain, and for reversing the process as peripheral cues of feeding are detected in another brain region.

Y4 receptors are an invaluable resource for drug design. The pancreatic polypeptide family is potentially involved in several pathophysiological conditions including memory loss, depression, anxiety, epileptic seizure, pain, depression, hypertension, locomotor problems, sleep disturbances, eating/body weight disorders, sexual/reproductive disorders, nasal congestion, and diarrhea (Wahlestedt et al., 1993; Dumont et al., 1992). The available data implicate this receptor in the control of obesity and other disorders of feeding including bulimia and anorexia. The chemical synthesis of selective drugs not only for Y4 but for all "Y type" receptors will be greatly accelerated by preliminary screening against a homogeneous population of cloned human Y4 receptors. As more specific pharmacological tools become available for probing receptor function, additional therapeutic indications are likely to be discovered.

We do not know whether hp25a represents the single Y4 receptor expressed in the human genome, or whether there exists a group of structurally related Y4 receptor subtypes. This is an issue which can be resolved using nucleotide sequence from hp25a as the basis for in situ localization, antisense or "knockout" strategies, homology cloning, and related techniques. Such approaches will enable us to investigate the existence of potentially novel receptor subtypes, in humans and other species, with pharmacologic and therapeutic significance.

In conclusion, the primary structure of the hp25a (Y4) gene, as well as its unique pharmacological profile obtained from transiently transfected cells, indicate that this gene encodes a new member of the pancreatic polypeptide receptor family. Additional cloning efforts will be required to isolate additional members of this newly recognized neuropeptide receptor family.

REFERENCES

Aakerlund, L., U. Gether, J. Fuhlendorff, T. W. Schwartz, and O. Thastrup. Y1 receptors for neuropeptide Y are coupled to mobilization of intracellular calcium and inhibition of adenylate cyclase. FEBS Lett. 260:73–78 (1990).

Alumets, J., R. Hakanson, and F. Sundler. Distribution, ontogeny and ultrastructure of pancreatic polypeptide (PP) cells in pancreas and gut of the chicken. Cell. Tissue Res. 194:377–386 (1978).

Beck, A. G., G. Jung, W. Gaida, H. Koppen, R. Lang, and G. Schnorrenberg. Highly potent and-small neuropeptide Y agonist obtained by linking $NPY_{1-4}$ via a spacer to alpha-helical $NPY_{25-36}$. FEBS Lett. 244: 119–122 (1989).

Beck-Sickinger, A. G., W. Gaida, G. Schnorrenberg, R. Lang, and G. Jung. Neuropeptide Y: Identification of the binding site. Int. J. Peptide Protein Res. 36: 522–530 (1990).

Bottcher, G., K. Sjolund, E. Ekblad, R. Hakanson, T. W. Schwartz, and F. Sundler. Co-existence of peptide YY in glicentin immunoreactivity in endocrine cells of the gut. Regul. Pept. 8:261–273 (1984).

Bradford, M. M. A rapid and sensitive method for the quantitation of microgram quantities of protein utilizing the principle of protein-dye binding. Anal. Biochem. 72:248–254 (1976).

Branchek, T., N. Adham, M. Macchi, H.-T. Kao, and P. R. Hartig. [$^3$H]-DOB (4-bromo-2,5-dimethoxyphenylisopropylamine) and [$^3$H]ketanserin label two affinity states of the cloned human 5-hydroxytryptamine$_2$ receptor. Mol. Pharmacol. 38:604–609 (1990).

Castan, I., P. Valet, T. Voisin, N. Quideau, M. Laburthe, and M. Lafontan. Identification and functional studies of a specific peptide YY-preferring receptor in dog adipocytes. Endocrinology 31:1970–1976 (1992).

Clark, J. T., P. S. Kalra, and S. P. Kalra. Neuropeptide Y stimulates feeding but inhibits sexual behavior in rats. Endocrinology 117:2435–2442 (1985).

De Wied, D. In: Neuropeptides: Basics and Perspectives (Elsevier, Amsterdam-New York-Oxford), 1990.

Heilig, M. and E. Widerlov. Neuropeptide Y: an overview of central distribution, functional aspects, and possible involvement of neuropsychiatric illnesses. Acta Psychiatr. Scand. 82:95–114 (1990).

Di Maggio, D. A., B. M. Chronwall, K. Buchman, and T. L. O'Donohue. Pancreatic polypeptide immunoreactivity in rat brain is actually neuropeptide Y. Neuroscience 15:1149–1157 (1985).

Dumont, Y., J.-C. Martel, A. Fournier, S. St.-Pierre, and R. Quiron. Neuropeptide Y and neuropeptide Y receptor subtypes in brain and peripheral tissues. Prog. Neurobiol. 38:125–167 (1992).

Eva, C., A. Oberto, R. Sprengel, and E. Genazzani. The murine NPY-1 receptor gene: structure and delineation of tissue specific expression. FEBS Lett. 314:285–288 (1992).

Eva, C., K. Keinanen, H. Monyer, P. Seeburg, and R. Sprengel. Molecular cloning of a novel G protein-coupled receptor that may belong to the neuropeptide receptor family. FEBS Lett. 271:80–84 (1990).

Fuhlendorff, J., N. Langeland Johansen, S. G. Melberg, H. Thogersen, and T. W. Schwartz. The antiparallel pancreatic polypeptide fold in the binding of neuropeptide Y to Y1 and Y2 receptors. J. Biol. Chem. 265:11706–11712 (1990).

Fuhlendorff, J., U. Gether, L. Aakerlund, N. Langeland-Johansen, H. Thogersen, S. G. Melberg, U. B. Olsen, O. Thastrup, and T. W. Schwartz. [Leu$^{31}$,Pro$^{34}$]Neuropeptide Y: A specific $Y_1$ receptor agonist. Proc. Natl. Acad. Sci. USA 87:182–186 (1990).

Glover, I. D., D. J. Barlow, J. E. Pitts, S. P. Wood, I. J. Tickle, T. L. Blundell, K. Tatemoto, J. R. Kimmel, A. Wollmer, W. Strassburger, and Y.-S. Zhang. Conformational studies of the pancreatic polypeptide hormone family. Eur. J. Biochem. 142:379–385 (1985).

Grundemar, L., S. P. Sheikh, and C. Wahlestedt, In: The Biology of Neuropeptide Y and Related Peptides. (Humana Press, Inc., Totawa, New Jersey), (1992).

Grundemar, L., J. L. Krstenansky, and R. Hakanson. Activation of neuropeptide Y1 and neuropeptide Y2 receptors by substituted and truncated neuropeptide Y analogs: identification of signal epitopes. Eur. J. Pharmacol. 232:271–278 (1992).

Herzog, H., Y. J. Hort, H. J. Ball, G. Hayes, J. Shine, and L. Selbie. Cloned human neuropeptide Y receptor couples to two different second messenger systems. Proc. Natl. Acad. Sci. USA 89:5794–5798 (1992).

Herzog, H., Y. J. Hort, J. Shine, and L. A. Selbie. Molecular Cloning, Characterization, and localization of the human homolog to the reported bovine NPY Y3 receptor: lack of NPY binding and activation. DNA and Cell Biology 12:465–471 (1993).

Hinson, J., C. Rauh, and J. Coupet. Neuropeptide Y stimulates inositol phospholipid hydrolysis in rat brain microprisms. Brain Res. 446:379–382 (1988).

Inui, A., M. Okita, M. Miura, Y. Hirosue, M. Nakajima, T. Inoue, and S. Baba. Characterization of the receptor for peptide-YY and avian pancreatic polypeptide in chicken and pig brains. Endocrinology 27:934–941 (1990).

Jazin, E. E., Yoo, H., Blomqvist, A. G., Yee, F., Weng, G., Walker, M. W., Salon, J., Larhammar, D., and Wahlestedt, C. A proposed bovine neuropeptide Y (NPY) receptor cDNA clone, or its human homologue, confers neither NPY binding sites nor NPY responsiveness on transfected cells. Reg. Peptides 47:247–258 (1993).

Jorgensen, J. C., J. Fuhlendorff, and T. W. Schwartz. Structure/function studies on neuropeptide Y and pancreatic polypeptide evidence for two PP-fold receptors in vas deferens. Eur. J. Pharmac. 186:105–114 (1990).

Laburthe, M. Peptide YY and neuropeptide Y in the gut: Availability, biological actions, and receptors. Trends Endocrinol. Metab. 1:168–174 (1990).

Laburthe, M., B. Chenut, C. Rouyer-Fessard, K. Taremoro, A. Couvineau, A. Servin, and B. Amiranoff. Interaction of peptide YY with rat intestinal epithelial plasma membranes: binding of the radioiodinated peptide. Endocrinology 118:1910–1917 (1986).

Larhammar, D. G., A. G. Blomqvist, F. Yee, E. E. Jazin, H. Yoo, and C. R. Wahlestedt. Cloning and functional expression of a human neuropeptide Y/peptide YY receptor of the Y1 type. J. Biol. Chem. 267:10935–10938 (1992).

Li, X. -J., Y. -N. Wu, R. A. North, and M. Forte. Cloning, functional expression, and developmental regulation of a neuropeptide Y receptor from drosophila melanogaster. J. Biol. Chem. 267:9–12 (1992).

Lundberg, J. M., A. Hemsen, O. Larsson, A. Rudehill, A. Saria, and B. Fredholm. Neuropeptide Y receptor in pig spleen: binding characteristics, reduction of cyclic AMP formation and calcium antagonist inhibition of vasoconstriction. Eur. J. Pharmacol. 145:21–29 (1988).

Mihara, S., Y. Shigeri, and M. Fujimoto. Neuropeptide Y-induced intracellular $Ca^{2+}$ increase in vascular smooth muscle cells. FEBS Lett. 259: 79–82 (1989).

Miller, J., and R. N. Germain. Efficient cell surface expression of class II MHC molecules in the absence of associated invariant chain. J. Exp. Med. 164:1478–1489 (1986).

Rimland, J., W. Xin, P. Sweetnam, K. Saijoh, E. J. Nestler, and R. S. Duman. Sequence and expression of a neuropeptide Y receptor cDNA. Mol. Pharmacol. 40:869–875 (1991).

Sambrook, J., Fritsch, E. F., and Maniatis, T., In: Molecular Cloning: A Laboratory Manual, 2nd Edition (Cold Spring Harbor Laboratory, Cold Spring Harbor, N.Y.), 1989.

Sanger, F., Nicklen, S. and Coulsen, A. R. Proc. Natl. Acad. Sci. USA 74:5463–5467 (1977).

Schwartz, T. W., S. P. Sheikh, and M. M. I. O'Hare. Receptors on pheochromocytoma cells for two members of the PP-fold family—NPY and PP. FEBS Lett. 225:209–214 (1987).

Schwartz, T. W. Pancreatic polypeptide a hormone under vagal control. Gastroenterology 85:1411–1425 (1983).

Schwartz, T. W., J. Fuhlendorff, L. L. Kjems, M. S. Kristensen, M. Vervelde, M. O'Hare, J. L. Krstenansky, and B. Bjornholm. Signal epitopes in the three-dimensional structure of neuropeptide Y. Ann. N.Y. Acad. Sci. 611:35–47 (1990).

Southern, E. M. Detection of specific sequences among DNA fragments separated by gel electrophoresis. J. Mol. Biol. 98:503–517 (1975).

Stanley, B. G., D. R. Daniel, A. S. Chin, and S. F. Leibowitz. Paraventricular nucleus injections of peptide YY and neuropeptide Y preferentially enhance carbohydrate ingestion. Peptides. 6:1205–1211 (1985).

Stanley, B. G., W. Magdalin, A. Seirafi, M. M. Nguyen, and S. F. Leibowitz. Evidence for neuropeptide Y mediation of eating produced by food deprivation and for a variant of the Y1 receptor mediating this peptide's effect. Peptides 13:581–587 (1992).

Voisin, T., M. Bens, F. Cluzeaud, A. Vandewalle, and M. Laburthe. Peptide YY receptors in the proximal tubule PKSV-PCT cell line derived from transgenic mice: relation with cell growth. J. Biol. Chem. 268:20547–20554 (1993).

Wahlestedt, C., and D. J. Reis. Neuropeptide Y-Related Peptides and Their Receptors-Are the Receptors Potential Therapeutic Targets? Ann. Rev. Pharmacol. Tox. 32: 309–352. (1993).

Wahlestedt, C., N. Yanaihara, and R. Hakanson. Evidence for different pre- and postjunctional receptors for neuropeptide Y and related peptides. Regul. Pept. 13:307–318 (1986).

Wahlestedt, C., Regunathan, S., and D. J. Reis. Identification of cultured cells selectively expressing Y1-, Y2-, or Y3-type receptors for neuropeptide Y/peptide YY. Life Sciences 50:PL-7-PL-12 (1991).

Wahlestedt, C., L. Edvinsson, E. Ekblad, and R. Hakanson. Effects of neuropeptide Y at sympathetic neuroeffector junctions: Existence of Y1 and Y2 receptors. In: Neuronal messengers in vascular function, Fernstrom Symp. No 10., (1990).
pp. 231–242. Eds A. Nobin and C. H. Owman. Elsevier:
Amsterdam (1987).

Whitcomb, D. C., I. L. Taylor, and S. R. Vigna. Characterization of saturable binding sites for circulating pancreatic polypeptide in rat brain. Am. J. Physiol. 259:G687–G691

---

What is claimed is:

1. An isolated nucleic acid molecule encoding a human Y4 receptor, wherein the Y4 receptor has the amino acid sequence shown in Sequence I.D. No. 2.

2. An isolated nucleic acid molecule of claim 1, wherein the nucleic acid molecule is a DNA molecule.

3. An isolated DNA molecule of claim 2, wherein the DNA molecule is a cDNA molecule.

4. A plasmid comprising the cDNA molecule of claim 3 adapted for expression in a mammalian cell which comprises the regulatory elements necessary for expression of the DNA in the mammalian cell operatively linked to the cDNA molecule so as to permit expression thereof, designated pcEXV-Y4 (ATCC Accession No. 75631).

5. An isolated DNA molecule of claim 2, wherein the DNA molecule is a genomic DNA molecule.

6. A vector comprising the DNA molecule of claim 2.

7. A plasmid comprising the vector of claim 6.

8. A plasmid of claim 7 adapted for expression in a mammalian cell which comprises the regulatory elements necessary for expression of the DNA in the mammalian cell operatively linked to the DNA encoding the Y4 receptor as to permit expression thereof.

9. A mammalian cell comprising the plasmid of claim 7.

10. A mammalian cell of claim 9, wherein the mammalian cell is a COS-7 cell.

11. A vector of claim 6 adapted for expression in a bacterial cell which comprises the regulatory elements necessary for expression of the DNA in the bacterial cell operatively linked to the DNA encoding the Y4 receptor as to permit expression thereof.

12. A vector of claim 6 adapted for expression in a yeast cell which comprises the regulatory elements necessary for expression of the DNA in the yeast cell operatively linked to the DNA encoding the Y4 receptor as to permit expression thereof.

13. A vector of claim 6 adapted for expression in an insect cell which comprises the regulatory elements necessary for expression of the DNA in the insect cell operatively linked to the DNA encoding the Y4 receptor as to permit expression thereof.

14. A vector of claim 6 adapted for expression in a mammalian cell which comprises the regulatory elements necessary for expression of the DNA in the mammalian cell operatively linked to the DNA encoding the Y4 receptor as to permit expression thereof.

15. An isolated nucleic acid molecule of claim 1, wherein the nucleic acid molecule is a RNA molecule.

16. A method of preparing an isolated Y4 receptor which comprises:

a. inserting the nucleic acid molecule of claim 1 into a suitable vector which comprises the regulatory elements necessary for expression of the nucleic acid operatively linked to the nucleic acid so as to permit expression thereof;

b. inserting the resulting vector into a suitable host cell so as to obtain a cell which expresses the nucleic acid and produces the receptor;

c. recovering the receptor produced by the resulting cell; and d. purifying the receptor so recovered.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1320 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 88..1212

( x i ) SEQUENCE DESCRIPTION: SEQ ID NO:1:

```
AGTATTGTTT  GTCTGTTGC  CTTGTAGGGC  GTCATCCCTC  AAGTGTATCA  CTTAGTTCAA                    60

GAGTCCTGGA  ATCTTTTCAC  ATCCACT ATG AAC ACC TCT CAC CTC CTG GCC                         111
                               Met Asn Thr Ser His Leu Leu Ala
                                1               5

TTG CTG CTC CCA AAA TCT CCA CAA GGT GAA AAC AGA AGC AAA CCC CTG                         159
Leu Leu Leu Pro Lys Ser Pro Gln Gly Glu Asn Arg Ser Lys Pro Leu
        10              15                  20

GGC ACC CCA TAC AAC TTC TCT GAA CAT TGC CAG GAT TCC GTG GAC GTG                         207
Gly Thr Pro Tyr Asn Phe Ser Glu His Cys Gln Asp Ser Val Asp Val
 25              30              35                          40

ATG GTC TTC ATC GTC ACT TCC TAC AGC ATT GAG ACT GTC GTG GGG GTC                         255
Met Val Phe Ile Val Thr Ser Tyr Ser Ile Glu Thr Val Val Gly Val
                 45              50                      55

CTG GGT AAC CTC TGC CTG ATG TGT GTG ACT GTG AGG CAG AAG GAG AAA                         303
Leu Gly Asn Leu Cys Leu Met Cys Val Thr Val Arg Gln Lys Glu Lys
             60                  65                  70

GCC AAC GTG ACC AAC CTG CTT ATC GCC AAC CTG GCC TTC TCT GAC TTC                         351
Ala Asn Val Thr Asn Leu Leu Ile Ala Asn Leu Ala Phe Ser Asp Phe
         75                  80                  85

CTC ATG TGC CTC CTC TGC CAG CCG CTG ACC GCC GTC TAC ACC ATC ATG                         399
Leu Met Cys Leu Leu Cys Gln Pro Leu Thr Ala Val Tyr Thr Ile Met
         90              95                  100

GAC TAC TGG ATC TTT GGA GAG ACC CTC TGC AAG ATG TCG GCC TTC ATC                         447
Asp Tyr Trp Ile Phe Gly Glu Thr Leu Cys Lys Met Ser Ala Phe Ile
105              110                 115                 120

CAG TGC ATG TCG GTG ACG GTC TCC ATC CTC TCG CTC GTC CTC GTG GCC                         495
Gln Cys Met Ser Val Thr Val Ser Ile Leu Ser Leu Val Leu Val Ala
                 125             130                 135

CTG GAG AGG CAT CAG CTC ATC ATC AAC CCA ACA GGC TGG AAG CCC AGC                         543
Leu Glu Arg His Gln Leu Ile Ile Asn Pro Thr Gly Trp Lys Pro Ser
             140                 145                 150

ATC TCA CAG GCC TAC CTG GGG ATT GTG CTC ATC TGG GTC ATT GCC TGT                         591
Ile Ser Gln Ala Tyr Leu Gly Ile Val Leu Ile Trp Val Ile Ala Cys
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 155 |     |     |     |     |     | 160 |     |     |     |     | 165 |     |      |
| GTC | CTC | TCC | CTG | CCC | TTC | CTG | GCC | AAC | AGC | ATC | CTG | GAG | AAT | GTC | TTC | 639  |
| Val | Leu | Ser | Leu | Pro | Phe | Leu | Ala | Asn | Ser | Ile | Leu | Glu | Asn | Val | Phe |      |
|     | 170 |     |     |     |     | 175 |     |     |     |     | 180 |     |     |     |     |      |
| CAC | AAG | AAC | CAC | TCC | AAG | GCT | CTG | GAG | TTC | CTG | GCA | GAT | AAG | GTG | GTC | 687  |
| His | Lys | Asn | His | Ser | Lys | Ala | Leu | Glu | Phe | Leu | Ala | Asp | Lys | Val | Val |      |
| 185 |     |     |     |     | 190 |     |     |     |     | 195 |     |     |     |     | 200 |      |
| TGT | ACC | GAG | TCC | TGG | CCA | CTG | GCT | CAC | CAC | CGC | ACC | ATC | TAC | ACC | ACC | 735  |
| Cys | Thr | Glu | Ser | Trp | Pro | Leu | Ala | His | His | Arg | Thr | Ile | Tyr | Thr | Thr |      |
|     |     |     |     | 205 |     |     |     |     | 210 |     |     |     |     | 215 |     |      |
| TTC | CTG | CTC | CTC | TTC | CAG | TAC | TGC | CTC | CCA | CTG | GGC | TTC | ATC | CTG | GTC | 783  |
| Phe | Leu | Leu | Leu | Phe | Gln | Tyr | Cys | Leu | Pro | Leu | Gly | Phe | Ile | Leu | Val |      |
|     |     |     | 220 |     |     |     |     | 225 |     |     |     |     | 230 |     |     |      |
| TGT | TAT | GCA | CGC | ATC | TAC | CGG | CGC | CTG | CAG | AGG | CAG | GGG | CGC | GTG | TTT | 831  |
| Cys | Tyr | Ala | Arg | Ile | Tyr | Arg | Arg | Leu | Gln | Arg | Gln | Gly | Arg | Val | Phe |      |
|     |     | 235 |     |     |     |     | 240 |     |     |     |     | 245 |     |     |     |      |
| CAC | AAG | GGC | ACC | TAC | AGC | TTG | CGA | GCT | GGG | CAC | ATG | AAG | CAG | GTC | AAT | 879  |
| His | Lys | Gly | Thr | Tyr | Ser | Leu | Arg | Ala | Gly | His | Met | Lys | Gln | Val | Asn |      |
|     | 250 |     |     |     |     | 255 |     |     |     |     | 260 |     |     |     |     |      |
| GTG | GTG | CTG | GTG | GTG | ATG | GTG | GTG | GCC | TTT | GCC | GTG | CTC | TGG | CTG | CCT | 927  |
| Val | Val | Leu | Val | Val | Met | Val | Val | Ala | Phe | Ala | Val | Leu | Trp | Leu | Pro |      |
| 265 |     |     |     |     | 270 |     |     |     |     | 275 |     |     |     |     | 280 |      |
| CTG | CAT | GTG | TTC | AAC | AGC | CTG | GAA | GAC | TGG | CAC | CAT | GAG | GCC | ATC | CCC | 975  |
| Leu | His | Val | Phe | Asn | Ser | Leu | Glu | Asp | Trp | His | His | Glu | Ala | Ile | Pro |      |
|     |     |     |     | 285 |     |     |     |     | 290 |     |     |     |     | 295 |     |      |
| ATC | TGC | CAC | GGG | AAC | CTC | ATC | TTC | TTA | GTG | TGC | CAC | TTG | CTT | GCC | ATG | 1023 |
| Ile | Cys | His | Gly | Asn | Leu | Ile | Phe | Leu | Val | Cys | His | Leu | Leu | Ala | Met |      |
|     |     |     | 300 |     |     |     |     | 305 |     |     |     |     | 310 |     |     |      |
| GCC | TCC | ACC | TGC | GTC | AAC | CCA | TTC | ATC | TAT | GGC | TTT | CTC | AAC | ACC | AAC | 1071 |
| Ala | Ser | Thr | Cys | Val | Asn | Pro | Phe | Ile | Tyr | Gly | Phe | Leu | Asn | Thr | Asn |      |
|     |     | 315 |     |     |     |     | 320 |     |     |     |     | 325 |     |     |     |      |
| TTC | AAG | AAG | GAG | ATC | AAG | GCC | CTG | GTG | CTG | ACT | TGC | CAG | CAG | AGC | GCC | 1119 |
| Phe | Lys | Lys | Glu | Ile | Lys | Ala | Leu | Val | Leu | Thr | Cys | Gln | Gln | Ser | Ala |      |
|     | 330 |     |     |     |     | 335 |     |     |     |     | 340 |     |     |     |     |      |
| CCC | CTG | GAG | GAG | TCG | GAG | CAT | CTG | CCC | CTG | TCC | ACA | GTA | CAT | ACG | GAA | 1167 |
| Pro | Leu | Glu | Glu | Ser | Glu | His | Leu | Pro | Leu | Ser | Thr | Val | His | Thr | Glu |      |
| 345 |     |     |     |     | 350 |     |     |     |     | 355 |     |     |     |     | 360 |      |
| GTC | TCC | AAA | GGG | TCC | CTG | AGG | CTA | AGT | GGC | AGG | TCC | AAT | CCC | ATT |     | 1212 |
| Val | Ser | Lys | Gly | Ser | Leu | Arg | Leu | Ser | Gly | Arg | Ser | Asn | Pro | Ile |     |      |
|     |     |     |     | 365 |     |     |     |     | 370 |     |     |     |     | 375 |     |      |

| TAACCAGGTC | TAGGTCTTCT | CCCTGCCATG | TCCCTTGCCA | GGCTCTTCCA | CTTAGCTAAG | 1272 |
|---|---|---|---|---|---|---|
| TGGGCACACT | GCAAGCTGGG | GTGGCACCCC | AGCATTCCTG | GCTTTCTG   |            | 1320 |

( 2 ) INFORMATION FOR SEQ ID NO:2:

( i ) SEQUENCE CHARACTERISTICS:
        ( A ) LENGTH: 375 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Asn | Thr | Ser | His | Leu | Leu | Ala | Leu | Leu | Leu | Pro | Lys | Ser | Pro | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gly | Glu | Asn | Arg | Ser | Lys | Pro | Leu | Gly | Thr | Pro | Tyr | Asn | Phe | Ser | Glu |
|     |     |     | 20  |     |     |     |     | 25  |     |     |     |     | 30  |     |     |
| His | Cys | Gln | Asp | Ser | Val | Asp | Val | Met | Val | Phe | Ile | Val | Thr | Ser | Tyr |
|     |     | 35  |     |     |     |     | 40  |     |     |     |     | 45  |     |     |     |
| Ser | Ile | Glu | Thr | Val | Val | Gly | Val | Leu | Gly | Asn | Leu | Cys | Leu | Met | Cys |

|  |  |  |  |  | 50 |  |  |  |  | 55 |  |  |  |  | 60 |  |  |
|---|---|---|---|---|---|---|---|---|---|---|---|---|---|---|---|---|---|
| Val<br>65 | Thr | Val | Arg | Gln | Lys<br>70 | Glu | Lys | Ala | Asn | Val<br>75 | Thr | Asn | Leu | Leu | Ile<br>80 |

Ala Asn Leu Ala Phe Ser Asp Phe Leu Met Cys Leu Leu Cys Gln Pro
                85                      90                  95

Leu Thr Ala Val Tyr Thr Ile Met Asp Tyr Trp Ile Phe Gly Glu Thr
            100             105                 110

Leu Cys Lys Met Ser Ala Phe Ile Gln Cys Met Ser Val Thr Val Ser
        115             120                 125

Ile Leu Ser Leu Val Leu Val Ala Leu Glu Arg His Gln Leu Ile Ile
    130             135                 140

Asn Pro Thr Gly Trp Lys Pro Ser Ile Ser Gln Ala Tyr Leu Gly Ile
145             150                 155                     160

Val Leu Ile Trp Val Ile Ala Cys Val Leu Ser Leu Pro Phe Leu Ala
            165             170                 175

Asn Ser Ile Leu Glu Asn Val Phe His Lys Asn His Ser Lys Ala Leu
            180             185                 190

Glu Phe Leu Ala Asp Lys Val Val Cys Thr Glu Ser Trp Pro Leu Ala
        195             200                 205

His His Arg Thr Ile Tyr Thr Thr Phe Leu Leu Leu Phe Gln Tyr Cys
    210             215                 220

Leu Pro Leu Gly Phe Ile Leu Val Cys Tyr Ala Arg Ile Tyr Arg Arg
225             230                 235                     240

Leu Gln Arg Gln Gly Arg Val Phe His Lys Gly Thr Tyr Ser Leu Arg
            245             250                 255

Ala Gly His Met Lys Gln Val Asn Val Val Leu Val Val Met Val Val
        260             265                 270

Ala Phe Ala Val Leu Trp Leu Pro Leu His Val Phe Asn Ser Leu Glu
        275             280                 285

Asp Trp His His Glu Ala Ile Pro Ile Cys His Gly Asn Leu Ile Phe
    290             295                 300

Leu Val Cys His Leu Leu Ala Met Ala Ser Thr Cys Val Asn Pro Phe
305             310                 315                     320

Ile Tyr Gly Phe Leu Asn Thr Asn Phe Lys Lys Glu Ile Lys Ala Leu
            325             330                 335

Val Leu Thr Cys Gln Gln Ser Ala Pro Leu Glu Glu Ser Glu His Leu
        340             345                 350

Pro Leu Ser Thr Val His Thr Glu Val Ser Lys Gly Ser Leu Arg Leu
        355             360                 365

Ser Gly Arg Ser Asn Pro Ile
    370             375

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

TTGCTTATGG GGCTGTGATT ATTCTTGGGG TCTCTGGAAA CCTGG        45

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:4:

TAGGATGATT ATGATCAATG CCAGGTTTCC AGAGACCCCA AGAAT        45

( 2 ) INFORMATION FOR SEQ ID NO:5:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

AAAGAGATGA GGAATGTCAC CAACATTCTG ATCGTGAACC TCTCC        45

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:6:

CAGCAAGTCT GAGAAGGAGA GGTTCACGAT CAGAATGTTG GTGAC        45

( 2 ) INFORMATION FOR SEQ ID NO:7:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

TGCAAACTGA ATCCTTTTGT GCAATGCGTC TCCATTACAG TATCCATTTT CTCT        54

( 2 ) INFORMATION FOR SEQ ID NO:8:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:8:

ACGTTCCACA GCGATGAGAA CCAGAGAGAA AATGGATACT GTAATGGAGA CGCA    54

( 2 ) INFORMATION FOR SEQ ID NO:9:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

CTGCAGTATT TTGGCCCACT CTGTTTCATA TTCATATGCT AC    42

( 2 ) INFORMATION FOR SEQ ID NO:10:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:10:

CAAGCGAATG TATATCTTGA AGTAGCATAT GAATATGAAA CA    42

( 2 ) INFORMATION FOR SEQ ID NO:11:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

CTGCTCTGCC ACCTCACGGC CATGATCTCC ACCTGCGTCA ACCCCATC    48

( 2 ) INFORMATION FOR SEQ ID NO:12:

( i ) SEQUENCE CHARACTERISTICS:
    ( A ) LENGTH: 48 base pairs
    ( B ) TYPE: nucleic acid
    ( C ) STRANDEDNESS: single (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:12:

GAAATTTTTG TTCAGGAATC CATAAAAGAT GGGGTTGACG CAGGTGGA 48